(12) United States Patent
Rice et al.

(10) Patent No.: US 10,648,964 B2
(45) Date of Patent: May 12, 2020

(54) BIOLOGIC STABILITY, DELIVERY LOGISTICS AND ADMINISTRATION OF TIME AND/OR TEMPERATURE SENSITIVE BIOLOGIC BASED MATERIALS

(71) Applicant: Biologistex CCM, LLC, Bothell, WA (US)

(72) Inventors: Michael Rice, Woodinville, WA (US); Bruce McCormick, Santa Fe, NM (US); Aby J. Mathew, Bothell, WA (US); Kevin O'Donnell, Arlington Heights, IL (US)

(73) Assignee: Biologistex CCM, LLC, Bothell, WA (US)

( * ) Notice: Subject to any disclaimer, the term of this patent is extended or adjusted under 35 U.S.C. 154(b) by 375 days.

(21) Appl. No.: 15/158,717

(22) Filed: May 19, 2016

(65) Prior Publication Data
US 2016/0338907 A1 Nov. 24, 2016

Related U.S. Application Data

(60) Provisional application No. 62/164,969, filed on May 21, 2015, provisional application No. 62/258,805, filed on Nov. 23, 2015.

(51) Int. Cl.
*B60C 23/00* (2006.01)
*G01N 33/483* (2006.01)
(Continued)

(52) U.S. Cl.
CPC ......... *G01N 33/483* (2013.01); *A01N 1/0273* (2013.01); *A61J 1/00* (2013.01);
(Continued)

(58) Field of Classification Search
None
See application file for complete search history.

(56) References Cited

U.S. PATENT DOCUMENTS 2,766,920 A 10/1956 Rawley
3,238,002 A 3/1966 O'Connell et al.
(Continued)

FOREIGN PATENT DOCUMENTS

WO 1994022233 A1 9/1994
WO 2010016768 A1 2/2010

OTHER PUBLICATIONS

Del Bo', et al., "Comparison of DNA damage by the comet assay in fresh versus cryopreserved peripheral blood mononuclear cells obtained following dietary intervention," Mutagenesis, 2015, 30, 29-35.

(Continued)

*Primary Examiner* — Adolf Dsouza
(74) *Attorney, Agent, or Firm* — Brown & Michaels, PC

(57) ABSTRACT

In some embodiments, alerts are sent to appropriate parties if an insulated container is not properly packed out to insure the approximate safe temperature of the materials. In other embodiments, a countdown timer is used to keep track of the time that the biologic has been in transit, and ensure that the amount of time does not exceed the known shelf life of the biologic. In still other embodiments, the payload container is equipped with its own sensors, such as temperature sensors, and communications devices, such as a close range communication device, capable of transmitting information regarding a range of parameters, including, but not limited to, temperature, humidity, location and time, from the payload container to an end user. In other embodiments, shielding and/or radiation sensors are included in insulated shipping or storage containers, or payload containers, to shield and monitor the radiation exposure of the payload.

19 Claims, 16 Drawing Sheets

(51) Int. Cl.
| | |
|---|---|
| *A61J 1/03* | (2006.01) |
| *A61J 1/00* | (2006.01) |
| *H04Q 9/00* | (2006.01) |
| *A01N 1/02* | (2006.01) |
| *B65D 43/02* | (2006.01) |
| *B65D 81/38* | (2006.01) |
| *G06Q 10/08* | (2012.01) |

(52) U.S. Cl.
CPC ................ *A61J 1/03* (2013.01); *B65D 43/02* (2013.01); *B65D 81/3813* (2013.01); *G06Q 10/0832* (2013.01); *H04Q 9/00* (2013.01); *A61J 2200/44* (2013.01); *A61J 2200/50* (2013.01); *A61J 2200/72* (2013.01); *A61J 2205/60* (2013.01); *B65D 2201/00* (2013.01); *B65D 2203/10* (2013.01); *H04Q 2209/40* (2013.01); *H04Q 2209/43* (2013.01); *H04Q 2209/823* (2013.01)

(56) References Cited

U.S. PATENT DOCUMENTS

| | | | | |
|---|---|---|---|---|
| 4,818,437 | A | | 4/1989 | Wiley |
| 5,274,239 | A | | 12/1993 | Lane et al. |
| 5,338,941 | A | | 8/1994 | Sappok |
| 5,924,302 | A | * | 7/1999 | Derifield ............ B65D 81/3862 62/371 |
| 6,045,990 | A | | 4/2000 | Baust et al. |
| 7,339,482 | B2 | | 3/2008 | Jaeger et al. |
| 7,622,921 | B2 | | 11/2009 | Fontius et al. |
| 8,061,149 | B1 | | 11/2011 | Gowans et al. |
| 8,154,421 | B2 | | 4/2012 | Saltzman et al. |
| 8,710,958 | B2 | | 4/2014 | Yang et al. |
| 8,872,627 | B2 | | 10/2014 | Davidowitz |
| 8,881,540 | B1 | | 11/2014 | Barakat et al. |
| 8,900,856 | B2 | | 12/2014 | Muller-Cohn et al. |
| 2005/0042144 | A1 | | 2/2005 | Hubbard |
| 2007/0109130 | A1 | | 5/2007 | Edenfield |
| 2007/0193297 | A1 | | 8/2007 | Wilson |
| 2008/0135564 | A1 | | 6/2008 | Romero |
| 2009/0102659 | A1 | | 4/2009 | Evans et al. |
| 2009/0109040 | A1 | | 4/2009 | MacLean et al. |
| 2010/0299278 | A1 | | 11/2010 | Kriss et al. |
| 2011/0279271 | A1 | | 11/2011 | Monroe |
| 2012/0053436 | A1 | | 3/2012 | Sauers et al. |
| 2013/0245991 | A1 | * | 9/2013 | Kriss ...................... G06Q 50/28 702/150 |
| 2014/0108027 | A1 | | 4/2014 | Greyshock et al. |
| 2014/0138392 | A1 | | 5/2014 | McCormick |
| 2014/0157797 | A1 | | 6/2014 | Kovalick et al. |
| 2014/0284503 | A1 | * | 9/2014 | Stevick ................... C22C 45/10 250/515.1 |
| 2015/0060686 | A1 | | 3/2015 | DeVolpi |
| 2016/0170072 | A1 | * | 6/2016 | Yaish ................... G01V 5/0008 702/179 |

OTHER PUBLICATIONS

Desouky, et al., "Targeted and non-targeted effects of ionizing radiation," Journal of Radiation Research and Applied Sciences, 2015, pp. 247-254.
Honda, et al., "Induction of Telomere Shortening and Replicative Senescence by Cryopreservation," Biochemical and Biophysical Research Communications, 2001, 282, 493-498.
Huang, et al., "Radiation-induced genomic instability and its implications for radiation carcinogenesis," Oncogene, 2003, 22, 5848-5854.
Kadhim, et al., "Non-targeted effects of ionizing radiation—implications for low dose risk," Mutat Res, 2013, 752(1): 84-98.
Xiang, et al., "Effects of anesthesia-induced modest hypothermia on cellular radiation sensitivity," Science in China (Series C), 2002, vol. 45, No. 1, 79-86.
Zhou, et al., "Induction of a bystander mutagenic effect of alpha particles in mammalian cells," PNAS, 2000, vol. 97 No. 5, 2099-2104.
Zhou, et al., "Interaction between Radiation-Induced Adaptive Response and Bystander Mutagenesis in Mammalian Cells," Radiat Res, 2003, 160(5): 512-516.
"EMF/RFI Shielding Coatings," www.tstcoatings.com/EMI_RFI_shielding.html, at least as early as Jul. 9, 2015.
"Radiation Detection Devices," http://www.remm.nlm.gov/civilian.htm, at least as early as Jul. 10, 2015.
SPD9441 Radiation Detector PIN Diode, Data Sheet #RC0130A, Solid State Devices, Inc., La Mirada, CA, http://www.ssdi-power.com/Resources/Documents/[300]SPD9441_DS.pdf, at least as early as Nov. 16, 2015.
TSA6G1 USB Mini Spectrum Analyzer, Data Sheet, Triarchy Technologies Corp., Surrey, British Columbia, http://www.triarchytech.com/Downloads/TSA6G/Datasheet_TSA6G1_11.pdf, at least as early as Nov. 16, 2015.
Electric Arc Spray, http://web.archive.org/web/20080509095536/http://www.tstcoatings.com/electric_arc_spray.html, May 9, 2008.
International Search Report and Written Opinion, International Application No. PCT/US2016/033418, dated Aug. 19, 2016.
Thermal Spray Processes, http://web.archive.org/web/20080509095706/http://www.tstcoatings.com/thermal_spray_processes.html, May 9, 2008.
About Thermal Spray Coatings in the Electrical and Electronics Industry, http://www.fst.nl/about/industry-solutions/thermal-spray-coatings-electrical-electronics-industry/, at least as early as Jan. 3, 2017.
Thermal Spray Coatings for Electronics, http://www.flamesprayusa.com/thermal-spray-coating-electronics.php, at least as early as Jan. 3, 2017.
International Search Report and Written Opinion, International Application No. PCT/US2016/033402, dated Sep. 28, 2016.
Hitemco SC-725 Technical Data Sheet, at least as early as 1985.
Hitemco SC-720AW Technical Data Sheet, at least as early as 1985.

* cited by examiner

Fig. 2A

PENDING SHIPMENTS

| RECIPIENT CLIENT | RECIPIENT CLIENT |
| Stem cells | Stem cells |
| RECIPIENT CLIENT | RECIPIENT CLIENT |
| Stem cells | Stem cells |

INCOMING SHIPMENTS

| RECIPIENT CLIENT | RECIPIENT CLIENT |
| 3:03am 04/27/15 | 1:18pm 04/27/15 |
| Stability Time Remaining | Stability Time Remaining |
| RECIPIENT CLIENT | RECIPIENT CLIENT |
| 10:03am 04/26/15 | 12:26pm 04/25/15 |
| Stability Time Remaining | Stability Time Remaining |

Last updated at 10:38am

| TRACKING NUMBER | RECIPIENT | CONTACT | STATUS |
|---|---|---|---|
| Z1472698357p | Johnson Biologics | James Franco | Awaiting carrier pickup |
| Z1472698357p | Merial | <Person Name> | In Transit |
| Z1472698357p | biotech1 | <Person Name> | In Transit |
| Z1472698357p | BioSolutions | <Person Name> | In Transit |
| Z1472698357p | Stem Cell Pros | <Person Name> | In Transit |
| Z1472698357p | Hutchinson | <Person Name> | In Transit |
| Z1472698357p | Stanley Treatments | <Person Name> | In Transit |
| Z1472698357p | Cancer Center Cures | <Person Name> | In Transit |
| Z1472698357p | 21st Century Medicine | <Person Name> | In Transit |
| Z1472698357p | LifeNet Solutions | <Person Name> | In Transit |
| Z1472698357p | CareCure | <Person Name> | In Transit |
| Z1472698357p | Global Biotech | <Person Name> | In Transit |

Fig. 2C

NEW SHIPMENT

- Shipment Info
- Set Alarms
- Choose Carrier

EVO Pack-out Time & Stability Period*

8 : 00 [am] on [04/15/15]

Stability period* [72] hrs

Review/Edit Configuration*

EVO Name/ID: [HAL 9000]

EVO Template/Config: 2-8C    change

Other Alarms

☑ Alert me if the EVO is opened before delivery

☑ Alert me when the EVO is within [5] miles of its destination

☑ Alert me when the EVO has not been delivered within [1] hours of stability period end ☑ Alert me when the EVO has been delivered but not opened within [1] hours of stability period end.

Send Alerts & Alarms To:    options

☑ Me
☑ Joan Chase
☑ James Franco
+ add contact number or email

*This must be entered to continue

[Next] [Cancel]

save for later

Fig. 2E

From:   To:   Status: Delivered

Shipper Name: (Org)

evo ID: _____    (Friendly) Name: _____

Details:

Pickup date & time: _____   Carrier: _____   Map1
Delivered @: _____   Tracking #: _____
Signed for by: _____   Shipment Info: _____   Map2

Alert Summary: _____

| Type | Date | Time | Parameter | Configuration | Value | Duration |
|---|---|---|---|---|---|---|
| Single Event | 1.1.15 | 10:26 am | Light | 0% | 100% | 5 min |
| Accumulated | 1.1.15 | 10:26 am | Temp. | 2-8C | 15C | 15 min |

Payload Temp Summary:

Temp Start Date (Day and Time):
Temp Finish Date (Day and Time):
Highest Temp:
Lowest Temp:
Average Temp:

Origin ◆——— dates/times ———▶ Destination

Shipment

00:18      39:19

Time of cold storage    packout    transit    delivery

Trip
00:00
Duration

BIOLOGIC STABILITY, DELIVERY LOGISTICS AND ADMINISTRATION OF TIME AND/OR TEMPERATURE SENSITIVE BIOLOGIC BASED MATERIALS

REFERENCE TO RELATED APPLICATIONS

This application claims one or more inventions which were disclosed in Provisional Application No. 62/164,969, filed May 21, 2015, entitled "BIOLOGICAL STABILITY, DELIVERY LOGISTICS AND ADMINISTRATION OF TIME AND/OR TEMPERATURE SENSITIVE BIOLOGIC BASED MATERIALS" and Provisional Application No. 62/258,805, filed Nov. 23, 2015, entitled "BIOLOGIC STABILITY, DELIVERY LOGISTICS AND ADMINISTRATION OF TIME AND/OR TEMPERATURE SENSITIVE BIOLOGIC BASED MATERIALS". The benefit under 35 USC § 119(e) of the United States provisional applications is hereby claimed, and the aforementioned applications are hereby incorporated herein by reference.

BACKGROUND OF THE INVENTION

Field of the Invention

The invention pertains to the field of transport and storage of biologic-based medicines and other biologics. More particularly, the invention pertains to biologic stability, delivery logistics and administration of time and/or temperatures sensitive medicines and other biologic based materials.

Description of Related Art

Most all biologic-based materials including medicines, vaccines, cell and gene therapies and engineered tissue products are subject to hypothermic storage of varying duration to attempt to ensure survival, recovery during an ex vivo storage interval, and return to normal biologic function following an ex vivo storage interval. All vaccines and 70% of biologics are temperature sensitive. Regenerative medicine therapies require precise thermal protection during shipment. Current methods deploy various insulated shipping containers, biopreservation media of varying formulas, and data loggers that record the container temperature and store this on fixed media.

Temperature sensitive biologic-based medicines and other biologics that are subjected to temperature excursions may suffer degradation so as to render them ineffective.

One of the common causes of temperature excursions in temperature sensitive packaging and shipping is due to failure of the pack out personnel to follow the prescribed procedures for packing out a shipment, resulting in pack out errors. In addition, traditional shipping containers have limited temperature stability.

The consequences of these errors can be extremely costly, when a biologic based medicine cannot be administered due to temperature excursions outside a validated temperature range, or if the shipment is delayed and the medicine cannot be administered once the dosage has exceeded its validated stability period. Cell viability declines or lost and unusable doses of the medicines are also possible. Administering a thermally sensitive biologic dose that was exposed to unknown temperature excursions, pack out errors or has exceeded it stability period is dangerous. Clinical impacts can potentially include the loss of life of a patient, who may be dependent on a biological, or temperature sensitive material achieving its desired therapeutic effect. Additional clinical impacts include negative impacts on clinical trial outcomes due to poor biologics management. There is also potentially a large economic burden from waste and scrapping of unusable biological materials due to errors in shipping.

An additional challenge for the successful shipment of a temperature sensitive material is the monitoring of the temperature and a range of other important parameters, which, if they vary outside of accepted and/or validated ranges, may harm the material being transported.

A further risk relating to the safe and proper handling of the shipment of these materials relates to the time window for use of the materials. Many biological materials may only be used for treatment within a specific time window, or stability period.

Prior art foam shipping containers such as extruded or expanded polystyrene have limited performance, can only be used a single time, and have a negative environmental impact. In addition, it is difficult to control the temperature in these containers.

Prior art vacuum panel shippers have a very large footprint, and are heavy. They also have a complicated assembly or pack out procedure and are expensive to ship. The insulating materials used in these shippers must be preconditioned to multiple temperature ranges prior to use.

U.S. Pat. No. 8,154,421, issued Apr. 10, 2012, entitled "REAL TIME TEMPERATURE AND LOCATION TRACKER", herein incorporated by reference, discloses a shipper having an outer housing with a temperature sensitive payload and a temperature/location tracker. The payload and temperature/location tracker are within a compartment of a body of the shipper. The temperature/location tracker has a first temperature probe, a GPS receiver, a cellular modem, and a GPS antenna. The tracker monitors and periodically transmits temperature and location values of the shipper over a cellular communication network.

Various causative agents, including radiation exposure, may also impact the viability and functionality of biologics. Biologics that are utilized for research and clinical applications (regenerative medicine, drug discovery, and biobanking) include, but are not limited to, cells or cell types that are generally shielded from natural and medical/industrial radiation by tissues, fat, bones, organs, etc. in their normal conditions. When packaged for therapeutic doses, these isolated cells and tissues are more vulnerable to radiation, and the impact of radiation exposure may result in lethal and sub-lethal cellular responses.

Lethal radiation, at the minimum of assessment parameters, results in failure of the biologic for its intended use. The loss of biologic integrity results in the biologic product not being utilized in the research or clinical application. The immediate consequences of lethal radiation would include loss of product for the patient or customer, loss of time in the clinical/research workflow, and/or loss of cost-of-goods and revenue. Generally, the recognition of altered product due to lethal radiation exposure would result in scrapped product and non-usage. Perhaps even more problematic would be the lack of recognition of negative impact to the biologic, which may result in usage within the research/clinical application. Negative consequences of use of the impacted biologic include patient reactions and altered research results.

Sub-lethal radiation can also cause alterations and altered activity in biologics. One risk with exposure to sub-lethal radiation is that biologic alterations may not be recognized via superficial assessment methods, and may be delayed in manifesting their alterations outside of routine assessment timing parameters. Furthermore, the biologic alterations from sub-lethal radiation may result in altered biologic responses that can vary from mild to extensive consequences. Protection from radiation that may result in sublethal exposure would also be beneficial for maintaining the integrity and quality of biologics.

Within regenerative medicine, drug discovery, and biobanking, cells and tissues may be of particular concern regarding radiation exposure, as their utility is related to maintenance of yield, viability, and functionality. Furthermore, lethal and sub-lethal radiation exposure can elicit cellular responses resulting in negative consequences beyond simple inactivation of the cell/tissue product. In addition, cells and tissues may be subjected to biopreservation steps (hypothermic preservation, cryopreservation) with inherent sensitivities that can instill cumulative stresses and sensitivities in combination with radiation exposure.

The effects of radiation in mammalian cells include, but are not limited to, gene mutation, chromosomal rearrangement, cellular transformation, cell death via apoptosis, necrosis, and secondary necrosis, and carcinogenesis. Deleterious effects of ionizing radiation (IR), including mutation and carcinogenesis, are due to cellular level damage, often at the point of the nuclear DNA via direct absorption of radiation energy, with surviving irradiated cells expressing alterations, and cell death of other cells resulting from direct cellular damage.

Radiation damage to the cell can be caused by the direct or indirect action of radiation on the DNA molecules. In direct action, the radiation disrupts the molecular structure of the DNA by targeting the DNA molecules directly. These disruptions lead to cell damage or cell death. Surviving damaged cells may later induce abnormalities or carcinogenesis. In indirect action, water molecules and other organic molecules in the cell (where free radicals such as hydroxyl and alkoxy are produced) are targets of the radiation. Since water makes up nearly 70% of the cell composition, most radiation induced damage results from indirect action. Direct and indirect effects cause biological and physiological alterations that may surface immediately or only after a prolonged period of time, such as decades or even longer. Specific cellular responses seen in response to low dose or low dose rate radiation include the radioadaptive response, the radiation-induced bystander response, low dose hyper-radiosensitivity, and genomic instability. (Desouky et al., "Targeted and Non-Targeted Effects of Ionizing Radiation", Journal of Radiation Research and Applied Sciences, 2015, pp. 247-254, herein incorporated by reference)

The deleterious effects of radiation can also occur in the progeny of irradiated cells after a delay. These deleterious effects are generally categorized as radiation-induced genomic instability (RIGI). Genomic instability is considered one of the most important aspects of cancer. (Huang et al., "Radiation-induced genomic instability and its implications for radiation", Oncogene (2003) 22, 5848-5854, herein incorporated by reference).

Humans and other organisms respond differently to low dose/low dose-rate radiation than they do to high dose/high dose-rate radiation. Non (DNA)-targeted effects include radiation-induced bystander effects (RIBE), genomic instability (GI), adaptive response, low dose hyperradiosensitivity (HRS), delayed reproductive death and induction of genes by radiation. "Non-targeted" effects do not require that nuclear DNA is directly exposed to irradiation to be expressed and they are particularly significant at low doses. Radiation-induced bystander effects (RIBE) are occurrences of biological effects in non-irradiated cells as a result of exposure of other cells in the population to radiation. Bystander effects have been mainly observed in high density cell cultures where only a small fraction of cells is irradiated. RIBE have been observed in DNA damage induction, the induction of mutations, micronuclei (MN) formation, sister chromatid exchanges (SCE), chromosomal instability (CIN), transformation, cell death (secondary necrosis or apoptosis), altered gene expression, differentiation, and alteration in the microRNAs (miRNAs) profile. One mechanisms of RIBE is gap-junction mediated intercellular communication (GJIC) which depends on the intercellular gap junctions' ability to transmit signals from irradiated to non-irradiated cells. (Desouky, 2015).

Radiation induced Genomic Instability (RIGI), observed in the progeny of irradiated cells, is a delayed appearance of de novo chromosomal aberrations, gene mutations and reproductive cell death. There is significant overlap between RIGI and the GI (genomic instability) observed in some (non-radiation-induced) cancers. Bone marrow cells irradiated with a low dose of ionizing high-LET alphaparticles (with a mean of one particle per traversed cell) resulted in significant expression of Chromosomal Instability (CIN) in vitro and in vivo. RIBE, observed in non-irradiated cells, may occur as a result of cells receiving signals from irradiated cells through gap junction communications or media from irradiated cells via diffusible factors. RIBE has been observed in a range of cell types, following a variety of radiation types and exposure procedures, particularly at low dose exposure. (Kadhim et al., "Non-targeted effects of ionizing radiation-implications for low dose risk", *Mutat Res.* 2013; 752(1): 84-98, herein incorporated by reference).

Irradiated cells may induce bystander mutagenic response in neighboring cells not directly exposed to radiation. (Zhou et al., Induction of a bystander mutagenic effect of alpha particles in mammalian cells", PNAS, 2000, vol. 97 no. 5, pp. 2099-2104, herein incorporated by reference). It is also noteworthy that bystander effects mediated via the surrounding media and gap junctions may also be mediated via the biopreservation media that is utilized for non-frozen preservation and cryopreservation of the cells and tissues. It is also possible that the composition of the biopreservation media may modulate the extent of radiation-induced cell damage. Intracellular-like biopreservation media has been shown to modulate biopreservation-induced cell damage and cell death (U.S. Pat. No. 6,045,990, herein incorporated by reference. Additionally, intracellular-like media has higher viscosity and generally contains high molecular weight components, in comparison to isotonic media, that may impede extracellular radiation-induced signaling factors that may result in bystander effects via media transfer and gap junction interactions.

Most cells being shipped or stored are subjected to hypothermic preservation or cryopreservation. Shipped cells may likely be exposed to some level of radiation during transport conditions and protocols. As discussed above, exposure to radiation during shipping/transport may be deleterious to cells. Furthermore, hypothermia and cryopreservation have the potential to have deleterious effects in isolation of radiation, and that might be noteworthy in combination with radiation exposure. Radiation-based DNA damage is potentially cumulative to, or amplification of, existing DNA damage from biopreservation of cells.

Hypothermia has been shown to enhance the radiation sensitivity of some cell types (Xiang et al., "Effects of anesthesia-induced modest hypothermia on cellular radiation sensitivity", Science in China (Series C), Vol. 45, No. 1, 2002, herein incorporated by reference). Cryopreservation significantly increased (up to 140%) DNA damage in cells compared with that observed in fresh samples. A source of antioxidants may also provide reduction in DNA damage. (Del Bo et al., "Comparison of DNA damage by the comet assay in fresh versus cryopreserved peripheral blood mononuclear cells obtained following dietary intervention", *Mutagenesis*, 2015, 30, 29-35, herein incorporated by reference).

Telomere shortening is related to cell aging, senescence, and onset of cell death. Cryopreservation generates single-strand breaks in telomeric DNA. An increase of single-strand DNA breaks in terminal restriction fragment (TRF) were found in cryopreserved cells after thawing. The rate of mean TRF length shortening was accelerated after cryopreservation. (Honda et al., "Induction of Telomere Shortening and Replicative Senescence by Cryopreservation", *Biochemical and Biophysical Research Communications* 282, 493-498, 2001, herein incorporated by reference).

Bystander effects cause damage in non-irradiated cells, which exaggerates the effect of low doses. There is also evidence of an adaptive response, where some cells exposed to low dose radiation have reduced sensitivity to subsequent stresses. (Zhou et al., "Interaction between Radiation-Induced Adaptive Response and Bystander Mutagenesis in Mammalian Cells", Radiat Res. 2003, 160(5): 512-516, herein incorporated by reference). This may cause cells intended to have transient therapeutic lifespans to remain in the body longer than intended, with continued activity, and/or be resistant to suicide switches to prevent progression into cancer cells or intended to inactivate cells causing Graft vs. Host Disease (GHVD) or cytokine overload. Although much focus is on the potential for radiation-induced effects resulting in cell damage or cell death, there is also concern for radiation-induced cellular changes that may result in pro-survival activity and proliferation beyond normal cell control mechanisms. Development of cell-based therapies takes into consideration the potential for cellular changes that result in cell degradation, but they also take into consideration the potential for uncontrolled cellular activity that may also lead to overall negative consequences for research and clinical applications.

SUMMARY OF THE INVENTION

In some embodiments, the biologic payload in a shipping or storage container is shielded from the radiated energy of a communications device by a shielding material in the shipping or storage container and/or in the payload container.

In other embodiments, sensors in the shipping or storage container and/or the payload container sense levels of radiation exposure in the containers. In some of these embodiments, the radiation being sensed is X-ray energy. In other embodiments, the radiation being sensed is radiation from a communications device within the shipping or storage container and/or the payload container, for example cellular radiation or RF energy.

An insulated shipping or storage container includes an insulated container body comprising a bottom and sidewalls extending from the bottom of the body, a first main cavity, and a second cavity, where the bottom and sidewalls form the first main cavity, and a removable top that fits onto the insulated container body, sealing the first main cavity. The shipping container also includes a long-range communications device located within the second cavity of the insulated container body, to transmit information to a communications network and a first shielding material lining at least a portion of the bottom and sidewalls of the insulated container body.

An insulated shipping or storage container includes an insulated container body comprising a bottom and sidewalls extending from the bottom of the body, a first main cavity and a second cavity, where the bottom and sidewalls form the first main cavity and a removable top that fits onto the insulated container body; sealing the first main cavity. The shipping container also includes a long-range communications device located within the second cavity of the insulated container body, to transmit information to a communications network and a shielding material lining at least a portion of the second cavity.

A payload container comprises shielding material lining at least a portion of a body of the payload container to protect the payload container from exposure to radiation.

BRIEF DESCRIPTION OF THE DRAWINGS

FIG. 2A shows a list of pending shipments, as well as the stability time remaining for shipments that have been recently delivered.

FIG. 2C shows an example of the pack out time and stability period being received into the system, as well as possible alert options.

FIG. 2E shows an example of a shipment report.

DETAILED DESCRIPTION OF THE INVENTION

Figure 1A:
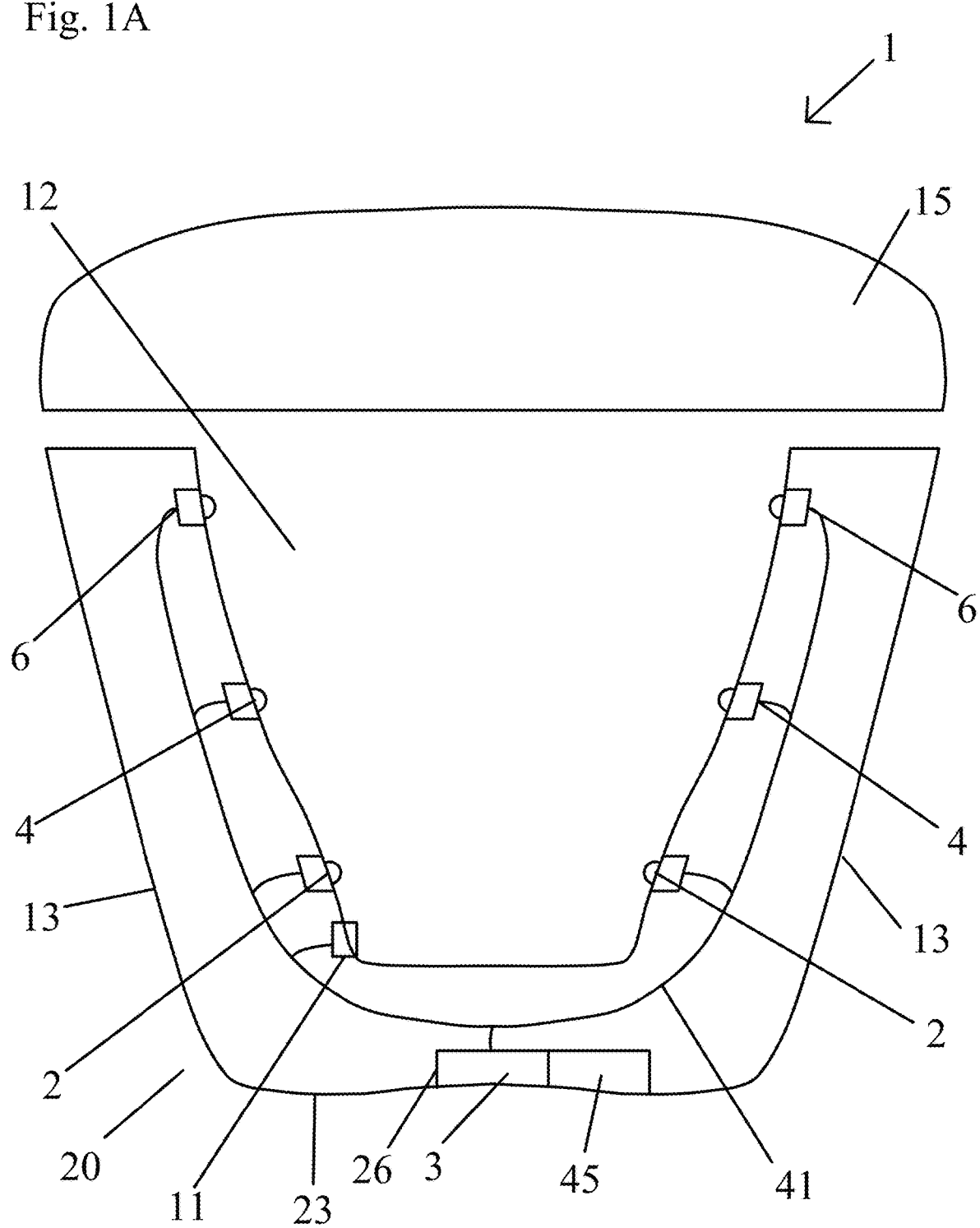
FIG. 1A shows an example of an empty insulated shipping container in an embodiment of the present invention.

Due to the critical nature of the temperature sensitive biologics, and the fact that a critical treatment may be awaiting the receipt of this shipment, it is extremely important that the status of the conditions of the shipment and its location are being reported in real time or near real time for review by the parties involved. There is a need in the art for real-time temperature monitoring and reporting during shipment.

There is also a need for a countdown timer to be available for all the interested parties to ensure that the biologic material is scheduled for use and used for treatment within a validated stability period.

There is also a need in the art to protect biologics from radiation exposure (both lethal and sub-lethal amounts), as well as sensing the extent of exposure of those biologics during storage and shipping. The methods and devices herein preferably protect the biologics from radiation that may result in non-lethal and/or lethal exposure, thus maintaining the integrity and quality of the biologics.

DNA damage mechanisms from both biopreservation and shipping radiation may be cumulative. Protective capabilities in both the biopreservation media and the shipping container would provide multiple mechanisms of protection. Therefore, improved shipping protection from radiation during shipping would reduce the risk of direct and indirect radiation-induced cell damage.

The methods and devices described herein provide people with better tools to manage the logistics of time sensitive materials and improve patient care.

"System", "tracking system", "logistics system", and "tracking/logistics system" are used interchangeably herein to indicate the logistics system that improves delivery logistics of the biologic being transported.

The present disclosure describes methods and devices to improve delivery logistics of time and/or temperature sensitive biologics. The containers described herein are thermally insulated containers intended for temporary storage of temperature-sensitive contents, such as biological or pharmaceutical products, during transport to a remote location. The containers are equipped with integrated electronics capable of measuring, storing, monitoring, tracking and communicating important information regarding the location of the container and the environment inside the container, where the temperature-sensitive contents are stored.

The containers are part of a logistics system and method of real-time monitoring of the location, internal temperature, and other parameters of the container or the biologics within the container. The integrated electronics are capable of broadcasting information regarding the container through the use of a global positioning system (GPS) and/or other wireless technologies, such as local area wireless communication (Wi-Fi), Bluetooth, cellular network, or other wireless networks.

In preferred embodiments, information regarding the container is wirelessly exchanged with cloud-based data storage or other communication networks. The container provides real-time and/or historical location and temperature data, as well as levels of radiation exposure, which can be processed and provided to customers or other users on multiple platforms in various formats. For example, the information from the container may be provided to users via mobile devices through short message service (SMS) and/or multimedia messaging service (MMS). In other embodiments, the information may be accessible via a cloud based database or from generated reports.

Embodiments of the present invention may be implemented in a cloud computing environment or with any other type of known or future developed computing environment.

A computer system/server may be utilized in distributed cloud computing environments where tasks are performed by remote processing devices linked through a communications network. In a distributed cloud computing environment, program modules may be located in both local and remote computer system storage media including memory storage devices. A computer system/server computer may also communicate with one or more external devices, such as device computers. The computer system/server computer typically includes a variety of computer system readable media. This media may be any available media that is accessible by computer system/server computer, and includes both volatile and non-volatile media, as well as removable and non-removable media.

Cloud computing enables convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

The container may also communicate information regarding the container itself (e.g. temperature information, location information, information regarding levels of radiation exposure) to a local user or network during non-transit periods.

In some embodiments, alerts are sent to appropriate parties if an insulated container is not properly packed out to insure the approximate safe temperature of the materials. In other embodiments, a countdown timer is used to keep track of the time that the biologic has been in transit, and ensure that the amount of time does not exceed the known shelf life of the biologic.

In still other embodiments, the payload container is equipped with its own sensors, such as temperature sensors or dosimeters to sense levels of radiation exposure, and with close range communication devices, capable of transmitting information regarding a range of parameters, including, but not limited to, temperature, humidity, location, levels of radiation exposure, and time, from the payload container to an end user via a mobile device application, the cloud hosted application, or another receiving system. Some close range communications devices that could be used include, but are not limited to, active RFID devices, RFID tags, RF transmitters, iBeacon™ transmitters, ZigBee® transmitters, Bluetooth transmitters, Wi-Fi radios, or other wireless transmitters.

The biologic based materials being transported may be any biological material, including, but not limited to, specimens, vaccines, medicines, pharmaceuticals, blood samples, cells, stem cells, tissues, engineered tissue products, manufactured cell and gene therapies, organs, or any fluid, bone or cellular or metabolic byproduct, intermediary, or derivative.

The insulated shipping container preferably includes sensors and/or switches to determine if an insulated container was packed out properly. The switches or sensors may include, but are not limited to, mechanical switches, magnetic switches, LED emitting detector pairs or other optical switches/sensors that project a beam of light at a particular wavelength, temperature sensors, pressure sensors, and/or other sensors including communication sensors that communicate with the insulated materials and payload container via any form of radio frequency (RF) communication.

The insulated materials, for example gel packs or cold packs, need to be placed in the insulated shipping container correctly in order to provide the correct temperature and temperature stability required for shipment. Similarly, the payload container (the container housing the biologic being transported) needs to be placed correctly. The payload container could be of any shape that can safely ship the biologic. The payload container could be a larger container preferably containing packing material to protect the payload from mechanical vibration, shock, or other forms of stress during transit. The larger payload container contains a smaller container, such as a vial, a specimen tube, a bag, or a syringe, that is in the larger container. In other embodiments, the payload container could be the container that actually houses the biologic.

The mechanical, magnetic or optical switches or sensors detect the presence or the absence of the required internal components of the shipping container. This is accomplished either physically (using the mechanical switches), magnetically (using reed switches/actuators in the magnetic switches), or optically (using light radiation of a certain wavelength). The temperature sensors, if present, also come into contact with the internal components to measure the temperature of those components.

The purpose of the switches/sensors is to prevent a biologic that was not packed correctly from being packed out and shipped. If the switches or sensors are not activated properly then the insulated container will utilize the embedded communications equipment to alert the appropriate parties prior to actual shipment of the container.

Optical sensors detect the presence or absence of the insulating materials (for example gel packs or ice packs) and the payload container when a light beam is broken. For mechanical switches, the actuator is physically moved by direct contact with the materials being packed. Reed switches or other actuators in magnetic switches are moved by a magnetic field. Temperature sensors verify that insulating materials have been pre-conditioned appropriately. For examples, gel packs change phase from liquid to solid at known temperatures and the suppliers or manufacturers instruct users to pre-condition these in a freezer or refrigerator for a minimum time duration. A temperature sensor in near proximity to a gel pack measures the temperature on the outside of the gel pack. If the gel pack is not at least at some minimum temperature, the sensor communicates that information to the computer, indicating that the gel pack is not ready. The computer can then alert the user of this problem, and/or block the shipment of the biologic until the proper temperature has been reached. The alert may include information that the particular gel pack should not be used. It also may include information that there is no confidence that the payload temperature will be maintained within a validated range and profile throughout the stability period.

In some embodiments, the insulated shipping container and/or the payload container include one or more temperature sensors. In embodiments where temperature sensors are used, they may come into contact with, be in direct contact with, or be in close proximity to whatever they are measuring in order to sense the temperature of that item or its environment. If the insulated materials being used in the packing were not conditioned or frozen sufficiently, these sensors alert a user regarding the improper preconditioning of the insulating materials, halting further packaging and shipping of the biologic until these errors are corrected.

The sensors are preferably at least partially embedded or fully embedded into one or more of the walls of an insulated shipping container. The sensors and switches indicate the proper placement of liquid, gel, or other insulating packs or materials and payload boxes or containers within the insulated shipping container. These sensors communicate either via hard wires or near field communication methods to a long-range communications device which itself is embedded into the body of the insulated shipping container. The long-range communications device may utilize cellular communication or other communication networks to communicate with a user. In some embodiments, a cellular modem is integrated into the communications device.

In some embodiments, sensors may also be embedded in the insulating materials, such as gel packs. In these embodiments, the sensors provide information to the logistics system regarding the presence, absence, and condition (e.g.—temperature) of the gel packs. In some embodiments, the sensor in the insulating material is an RFID tag, a temperature sensor, or a magnet.

The logistics/tracking system may contain the ability to complete shipping air bills, and communicate with appropriate users as to the status and location of a particular shipping container. The logistics/tracking system may also prevent the completion of an air bill if the pack out procedures are not properly followed, resulting in activation of the built in sensors and/or switches. The logistics/tracking system may be cloud-based, a client application, and/or a mobile application.

There are potential deleterious effect of radiated radio frequency and other energy sources on mammalian cells, tissues, organs, and species. In some embodiments, methods and devices described herein protect biologic payloads (for example, cells and tissues) from these energy sources, some of which are used to monitor payload status as described herein.

In preferred embodiments described herein, the communications device in the shipping or storage container is a long-range communications device such as a cellular device for cloud or other communication and also preferably uses near field electronic communication to provide information and may communicate using iBeacon™, Zigbee®, Bluetooth®, Wi-Fi or other forms of near field communication (NFC). In these methods and devices, the communication devices may transmit information to other devices utilizing near field communication methods. Some examples of these communications devices include, but are not limited to, cellular communication devices (e.g.—cellular phones, cellular modems, code division multiple access systems, global system for mobile communications, and other cellular portions of the spectrum), RF transmitters, active RFID devices, RFID tags, iBeacon™ transmitters, ZigBee® transmitters, Bluetooth® transmitters, Wi-Fi radios, other wireless transmitters, or other near field communication signals or devices.

In some embodiments with a communications device in the payload container, the communications device in the payload container is a near field communication device that provides information and may communicate, for example with the shipping or storage container or a smartphone device, using low power communications including Bluetooth®, iBeacon™, ZigBee®, Wi-Fi or other forms of near field communication (NFC).

In some embodiments, insulation or attenuation shielding materials are added to shipping or storage containers to limit exposure of biologic payloads in various shipping or storage containers to radiated energy (ionizing radiation or non-ionizing radiation) from embedded or nearby communications devices. In some embodiments, the materials attenuate ionizing radiation (e.g.—X-ray radiation such as airport screening devices).

In some embodiments, methods and devices herein use sensors, communication devices, and software to measure and report non-inoizing radiated energy exposure of the biologic payload inside a shipping or storage (non transported) container.

In other embodiments, methods and devices herein use sensors, communication devices and software to measure and report any ionizing radiation, such as X-ray energy, that gets to the biologic payload inside a shipping or storage (non-transported) container.

In some embodiments, the biologic payload in a shipping or storage container is shielded from the non-ionizing radiated energy of the communications device. The shielding may be made of any material that effectively blocks radiation from the communications device including, but not limited to, lead, aluminum, bronze, copper, nickel, zinc, another metal, conductive plastics, or carbon based materials.

One way to shield the payload container is to use a plate in the electronics cavity that still permits the communications device, to transmit. In some embodiments, the plates are made from lead, aluminum, bronze, copper, nickel, zinc, another metal, conductive plastics, or carbon based materials. The plate is preferably placed in the electronics cavity, or in another location between the communications device and the payload container. Another way to shield the payload container uses a coating, for example a sprayed shielding such as a coating applied with an electric arc spray gun. In some preferred embodiments, the coating is an electric arc sprayed zinc coating. The coating could be applied to an interior of a liner between the communications device and the payload container. In one preferred embodiment, a metallic coating is sprayed on the underside of a liner using an electric arc spray gun. The coating could alternatively be applied directly to the interior or exterior surface of the shipping container. Alternatively or additionally, the coating could be applied to the interior and/or exterior surface of the payload container itself. In some embodiments, the coating may be made from lead, aluminum, bronze, copper, nickel, zinc, another metal, conductive plastics, or carbon based materials. The coatings chosen are preferably made of materials that allow X-rays to pass through so that all interior spaces of the shipping container are still visible.

In other embodiments, the shielding may be inserts, sprayed on liners, mesh, foil, foam, paints, inks, solid plates or pieces, or a film adhesive. In these embodiments, the shielding is made from lead, aluminum, bronze, copper, nickel, zinc, another metal, conductive plastics, or carbon based materials.

In some embodiments, methods and devices use sensors, communication devices and software to measure and report any exposure of the biologic payload inside a shipping or storage (nontransported) container to non-ionizing radiation (such as radio frequency energy from cellular modems or other communication devices). In some embodiments with shielding, a sensor is included within the payload container. The sensor could be inside the payload container, or integrated within the body of the payload container. For example, a radiation detector of various embodiments. One such radiation detector is a modular device with a wired sensor incorporating a radiation detector diode (such as the SPD9441 Radiation Detector PIN Diode, Solid State Devices, Inc., La Mirada, Calif., http://www.ssdi-power.com/Resources/Documents/[300]SPD9441_DS.pdf, herein incorporated by reference). The shipping containers and payload containers may be tested prior to use to assess how much electromagnetic radiation gets into the containers and what levels prevent cloud communication. As another example, a spectrum analyzer with an antenna in the payload cavity could collect all of the radiation data. This could also indicate whether signal strength from the communications device is sufficient to properly transmit data from the shipping container to the cloud and other external receivers. Another example is a USB spectrum analyzer for detecting and measuring emitted electromagnetic radiation from cell phones or other sources (such as the TSA6G1 USB Mini Spectrum Analyzer, Triarchy Technologies Corp., Surrey, British Columbia, http://www.triarchytech.com/Downloads/TSA6G/Datasheet_TSA6G1_11.pdf, herein incorporated by reference).

In some embodiments, methods and devices use sensors, communication devices and software to measure and report any ionizing radiation, including X-ray energy, that gets to the biologic payload inside a shipping or storage container (non-transported). Sensors to detect radiation levels may be used to detect levels of X-ray exposure (with or without shielding). Some examples are small form factor ionization detector chips and sensors that could be embedded in a shipping container. Another example is a modular device with a wired sensor incorporating a radiation detector diode (such as the SPD9441 Radiation Detector PIN Diode, Solid State Devices, Inc., La Mirada, Calif.). This would capture data on payload exposure to X-rays. This data would be useful in determining the level of exposure of the biological payload during transport. Real time or near real time monitoring of X-ray energy on mammalian cells also enables longitudinal studies on impact of cell viability and function following exposure Improved shielding methods protect the biologic payload from deleterious energy sources. The X-ray sensor may be wired or wireless and communicates with the communications device (e.g.—near field transmitter or cell modem) to get the data externally transmitted (e.g.—to the cloud).

An example of an insulated shipping container 1 with sensors/switches 2, 4, 6 is shown in FIGS. 1A and 1B. The insulated shipping container 1 may also optionally contain one or more temperature sensors 11 such as thermocouples. While there is only one temperature sensor 11 shown in FIG. 1B, multiple temperature sensors 11 may be present in different locations throughout the insulated shipping container 1. Depending upon their locations, the temperature sensors could monitor the temperature of any of the materials (top or bottom insulating material or payload container) in the insulated shipping container. The temperature sensors 11 are preferably connected to the communications device 3 via hard wiring. In alternative embodiments, the temperature sensors 11 are wirelessly connected to the communications device 3.

The insulated shipping container 1 includes a bottom or body 20 and a top or lid 15. The body 20 includes a base 23 and sidewalls 13 that extend up from the base 23. The body 20 defines an open storage volume or cavity 12. The top 15 is removable to provide access to the storage volume 12. When the top 15 is placed on the body 20, the storage volume 12 is closed. The top 15, the base 23 and the sidewalls 13 preferably include multiple layers of insulating materials.

In some preferred embodiments, the layers of insulating materials forming the body 20 and top 15 of the insulated shipping container include an aerogel layer and a foam layer sandwiched between and in contact with inner and outer plastic layers. In some examples, the plastic layers are preferably ABS (Acrylonitrile Butadiene Styrene) plastic layers. The outer and/or inner plastic layers may also preferably be covered with an EVA (ethylene vinyl acetate) material layer. Other insulating materials for the body and top of the insulated shipping container, as known in the art, may alternatively be used.

The payload container 8 is placed between the insulated materials 5 and 7 in the inner cavity 12 of the insulated shipping container 1. The sensors 2, 4, 6 are preferably embedded into one or more of the sidewalls 13 of the insulated shipping container 1. The sensors may be partially or fully embedded into the sidewalls 13. The switches or sensors 2, 4, 6 are preferably located in the shipping container 1 at locations where they can sense the location and placement of the insulation materials 5 and 7, and the payload container 8, which houses the biologic. In preferred embodiments, the payload container 8 also includes a communications device 9 and/or a temperature sensor 10 (shown in FIG. 3B).

Figure 1B:
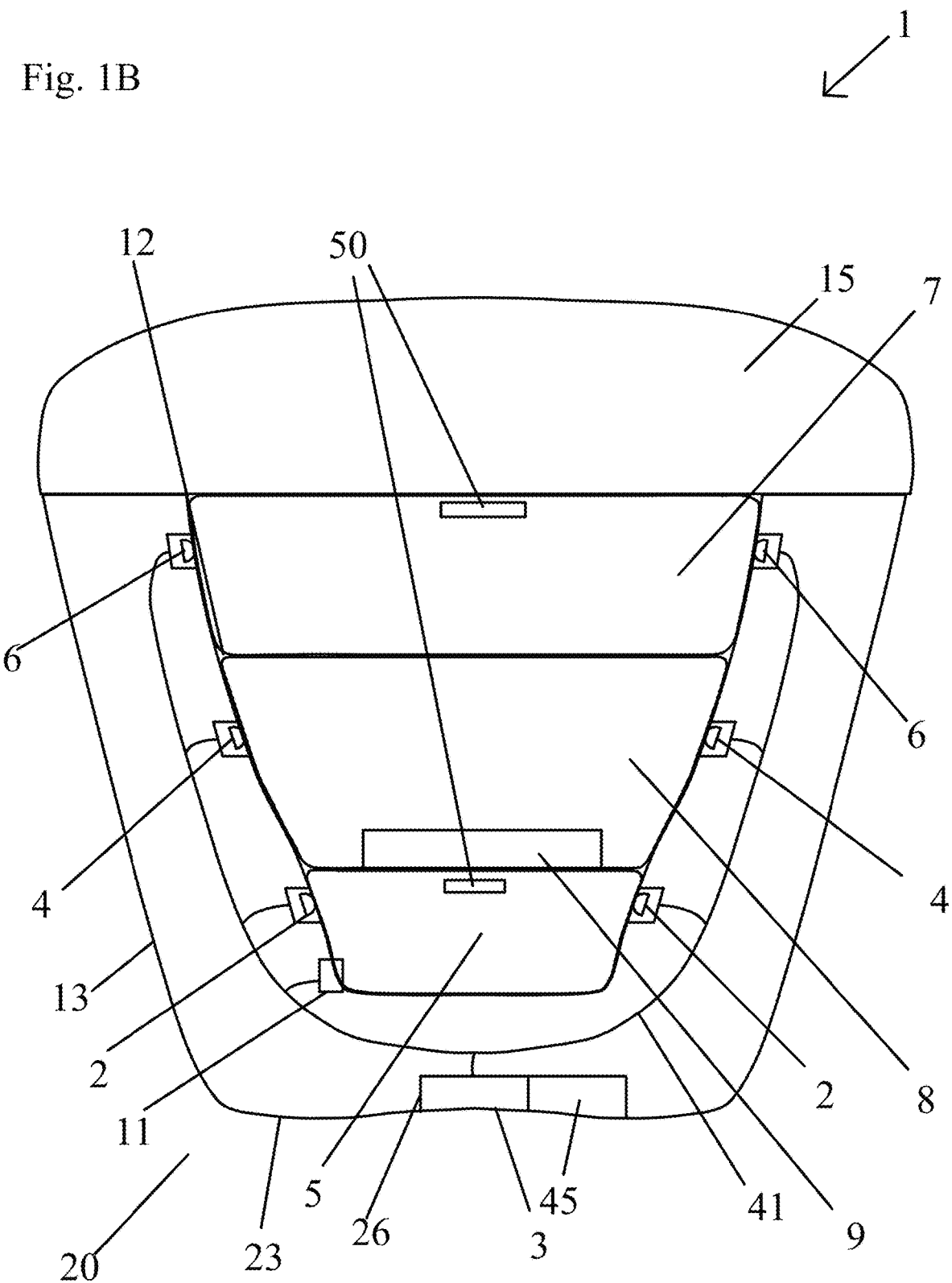
FIG. 1B shows the insulated shipping container of FIG. 1A, packed with insulating materials and the payload container and examples of locations for the switches and/or sensors in the shipping container.

FIGS. 1A and 1B show an example of a configuration of the sensors and switches where the switches or sensors 2 sense the insulation material 5, switches or sensors 4 sense the payload container 8, and switches or sensors 6 sense the insulation material 7. Additional switches or sensors 2, 4, 6, may be included to increase the sensing accuracy regarding conditions of the biologic.

At least one communications device 3 is preferably placed in the shipping container 1. The communications device 3 is preferably housed in a cavity 26 in the base 23 of the insulated shipping container 1. In some embodiments, the communications device 3 includes GPS, a cellular modem, and/or other wireless communication devices. The wireless communication devices are preferably permanently integrated into the base 23 of the container 1.

The insulated shipping container 1 also preferably includes a power compartment 45, which provides power to the electronics in the insulated shipping container 1. In some preferred embodiments, the power compartment 45 is a battery compartment 45, which contains a battery pack. The battery pack preferably powers the communications device 3. While the power compartment 45 is shown on the bottom of the insulated shipping container 1 in the Figures, the power compartment 45 may be in alternative locations, and is preferably connected (via wiring) to the communications device 3.

The sensors/switches 2, 4, 6 are preferably connected to the communications device 3 so that the information from the sensors/switches 2, 4, 6 is transmitted to the communications device 3. In some embodiments, as shown in FIGS. 1A and 1B, the sensors/switches are connected to the communications device 3 using wiring 41. In other embodiments, the sensors and/or switches are wirelessly connected to the communications device 3.

The communications device 3 permits the insulated shipping container to communicate to an outside source, including, but not limited to, a cloud-based database or program, device computers, server computers, or other devices. It should be noted that the term "outside" means with a device other than present within the shipping container. While the communications device 3 is shown placed in the base 23 of the shipping container 1 in FIGS. 1A and 1B, the communications device may be in any location where it does not interfere with the switches/sensors.

This communication device 3 communicates to an outside source including, but not limited to, a cloud-based database or program, device computers, server computers, or other devices. The outside source can also determine whether certain parameters are not within appropriate ranges and notify users. The tracking system also can be utilized to complete shipping air bills and as a result, if the switches are activated, prevent the completion of an air bill, which effectively will prevent an improperly packaged shipment from being shipped.

In some embodiments, sensors 47, 50 may also be embedded in the insulating materials 5, 7, such as gel packs. In these embodiments, the sensors provide information to the logistics system regarding the presence, absence, and condition (e.g.—temperature) of the gel packs. In some embodiments, the sensor/switch is an RFID tag, a temperature sensor, or a magnet. FIGS. 1A and 1B show an example of an RFID tag 50 or temperature sensor in one of the insulating materials.

Figure 1C:
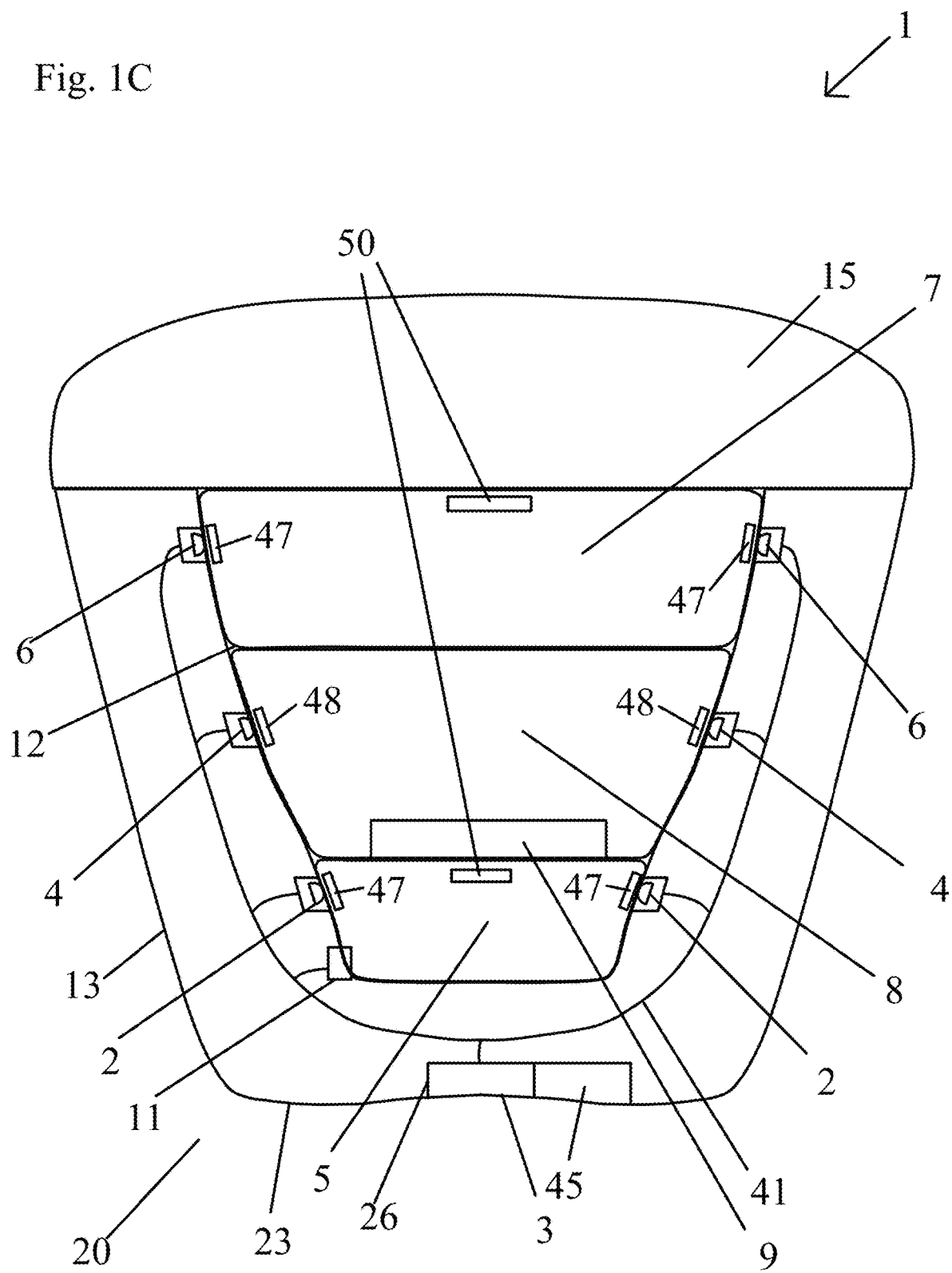
FIG. 1C shows an embodiment of an insulated shipping container, using magnetic switches.

FIG. 1C shows an embodiment of a packed insulating shipping container 1, where the gel packs 5 and 7, and the payload container 8, include magnets or metallic materials 47, 48. In this embodiment, the sensors/switches 2, 4, 6 are magnetic switches. The magnetic switches 2, 6 interact with the magnets 47 in the gel packs, while the magnetic switches 4 interact with the magnets 48 in the payload container. When properly packed, this interaction indicates that the insulated shipping container 1 is ready for shipping and this information is preferably received by the logistics system. If the magnets or metallic materials 47, 48 are not properly lined up with the magnetic switches 2, 4, 6 in the insulated shipping container 1, the insulated shipping container has not been properly packed and this information is preferably received by the logistics system.

The tracking system receives the type of shipping container used to ship the biologic. The tracking system receives data from the sensors within the insulated shipping container. The tracking system determines whether the shipping container was properly packed based on the information from the sensors. If the shipping container was not properly packed, then the tracking system prevents a shipping bill from being completed and may send a message to a designated user. If the shipping container was properly packed, the computer releases the insulated shipping container for shipping to its destination.

Proper packing of the shipping container occurs when a bottom insulating material (such as an ice pack or a gel pack) is accurately placed in the insulated shipping container, the payload container is next accurately placed in the shipping container, and the top insulating material (such as an ice pack or a gel pack) is accurately placed on top of the payload container.

The tracking/logistics system is accessed and the shipping container is selected from a list of shipping containers. The system verifies whether the bottom insulating material, the payload container and the top insulating material are properly placed based on the information received from the sensors/switches in the shipping container. The tracking/logistics system also preferably verifies whether the insulation materials or gel packs are within an acceptable starting temperature range. If the system has verified that the materials have been packed correctly and, in embodiments with a temperature sensor, are within an acceptable starting temperature range, the tracking system will permit proceeding to the next step in the shipping process. If the tracking system reports that the packing procedure has not been performed correctly, the user is not permitted to continue with the shipping process. The operator must inspect the shipping container to ensure that it is packed out correctly with the required components.

In preferred embodiments, once the package is approved for shipping, the user enters the time the shipping container was loaded (the "pack out time") and the stability period for the biologic (or "payload") in the payload container into the tracking/logistics system. The user may configure specific alert messages to various recipients regarding the shipment location, arrival at destination, and time remaining in a stability countdown timer. The computer receives the pack out time and the stability period, and begins to countdown the stability period once it receives that information. The computer may also send alerts regarding the countdown timer and the stability period to one or more users.

The countdown timer is activated within the tracking system, which is in communication with a shipping container. A stability countdown timer may be displayed by the tracking/logistics system and is activated once the computer receives values for the pack out day and time and the stability period. Once activated, the countdown timer alerts the appropriate parties who have been entered as alert recipients in the tracking system. Periodic updated alerts may also be programmed and communicated to recipients via e-mail messages and SMS.

Figure 2B:
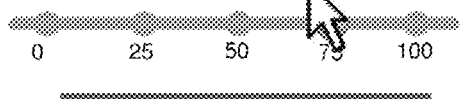
FIG. 2B shows parameters being monitored and when alarms may be sent if those parameters are outside certain ranges. The numeric ranges and values displayed are for illustrative purposes only. The actual values depend upon many factors, including, but not limited to, the biologic being shipped and the distance and time of transport.
Figure 2B:
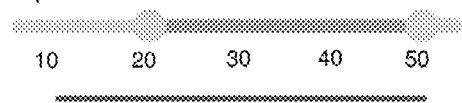
Figure 2B:
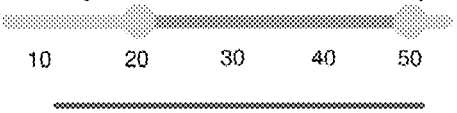
Figure 2B:
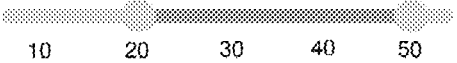

The tracking system also may communicate location data, which may be communicated by the long-range communications to the tracking system, along with the time left on the stability countdown timer. FIGS. 2A through 2E show examples of information in the logistics system. The alerts provide real time locations (e.g. ~5 miles from destination) and can be acted upon based on those locations. Some examples for alerts are shown in FIG. 2C.

Figure 2D:
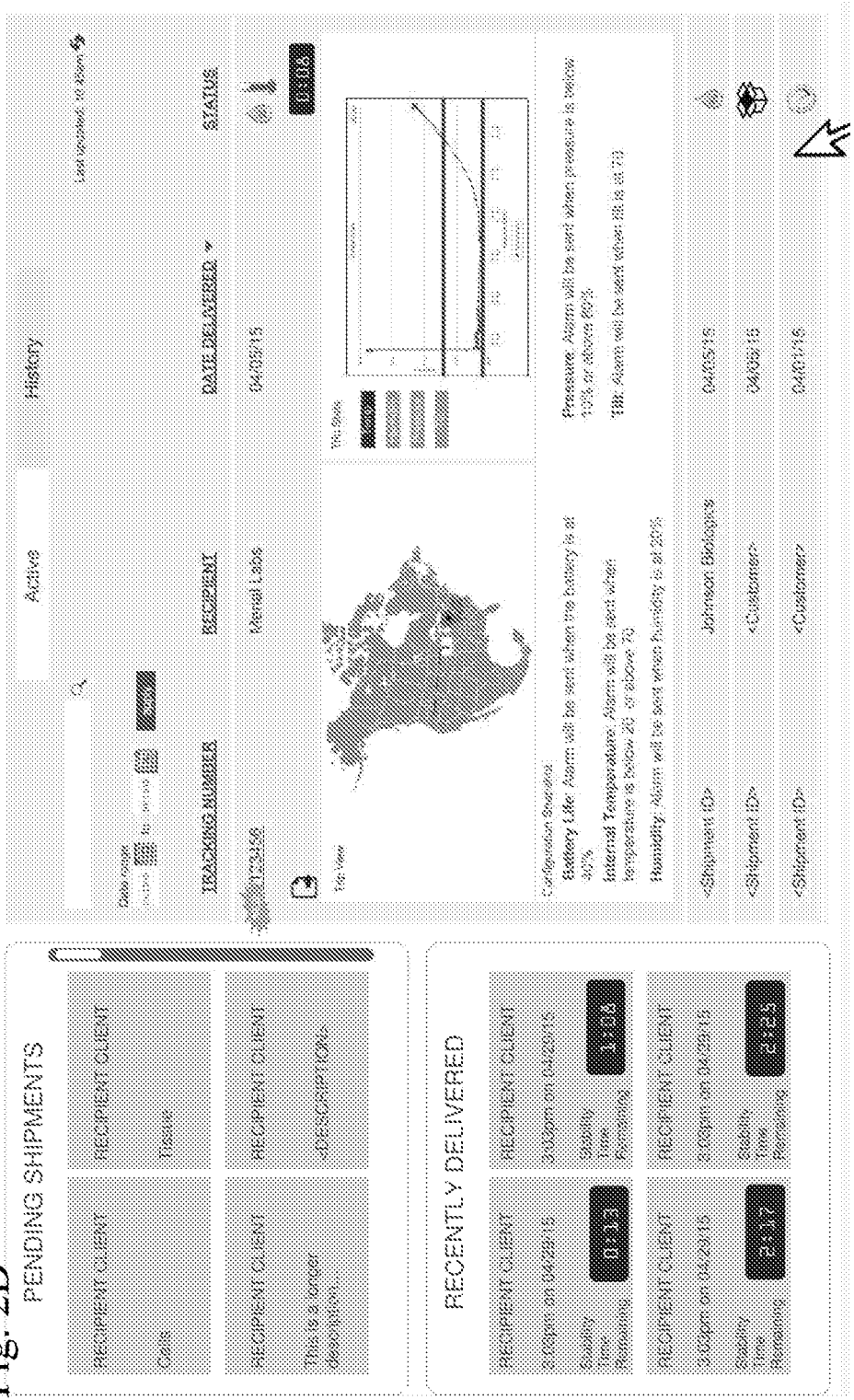
FIG. 2D shows information on pending shipments, recently delivered biologic shipments (with stability time remaining) and other parameters.

FIG. 2C shows an example of a pack-out time and stability period that has been received by the computer. FIG. 2D shows stability countdown timers for recently delivered shipments, with the stability time remaining. The countdown timer continues to run once the shipment has been delivered, to keep all users aware of the continued need to get the time and/or temperature sensitive biologic material to the actual recipient.

Many biologics have very short shelf lives, which makes it very difficult to ship them around the world. Also, there are often delays in shipping, which would make a biologic no longer viable when it reaches its destination. The addition of a stability countdown timer permits anyone interested in the amount of time the biologic has been in transport, to obtain the amount of time left for the biologic being shipped to be viable. Therefore, this method is able to calculate how much time is left in the viability/stability period.

Once the computer receives the pack out time and stability period, the time left in the stability period is calculated and the computer begins the countdown. By monitoring the stability time period, there is an increase in the awareness regarding where the package is and how that affects the stability and viability of the biologic being transported.

Throughout transport of the shipment, the alerts as to the location of the container, as well as the amount of time left on the countdown timer, may be sent to the designated recipients. The information about when the container was delivered may also be preferably provided to the designated recipients. Since many medicines or other biologics need to be used within a validated protocol time period, this information is crucial in the decision making processes of clinicians and other practitioners once the biologic is received and for clinical administration purposes.

Information from the countdown timer may be sent to one or more users. The computer may display it in a preconfigured app, or the user may log in to access the current status of the countdown timer. When the countdown timer is reviewed, the computer displays to the user the amount of time left, and where the container is. If there is a delay during transit that would adversely affect the biologic, the user can utilize this information to determine whether the biologic could still be transported in an alternative manner while maintaining stability, aiding in making decisions about alternative transport.

In a first step of monitoring a stability countdown timer of a shipment, the pack out time is received by a tracking system. The shelf life/stability period of the particular biologic being shipped is also preferably received by the system. During transit of the shipment, the tracking system may provide users access to the time remaining in the stability period. The tracking system may send alerts regarding the time remaining on the stability countdown timer. These alerts may be sent via e-mail, SMS, MMS, or other methods. By monitoring the stability period of a biologic during transport, the delivery and administration time and/or temperature sensitive medicines to the patient or laboratory can be closely monitored and evaluated.

Figure 3A:
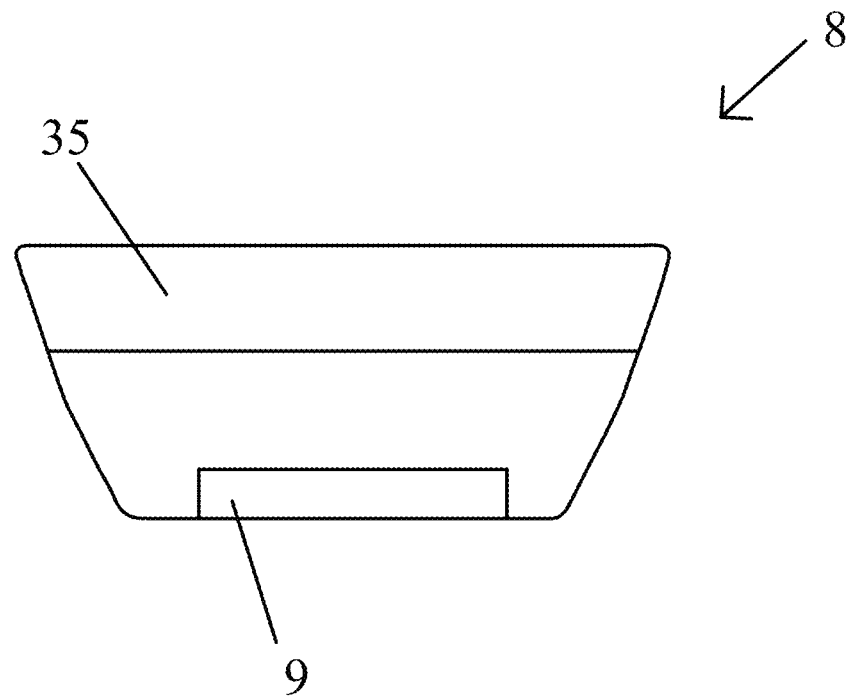
FIG. 3A shows an example of a payload container in an embodiment of the present invention.
Figure 3B:
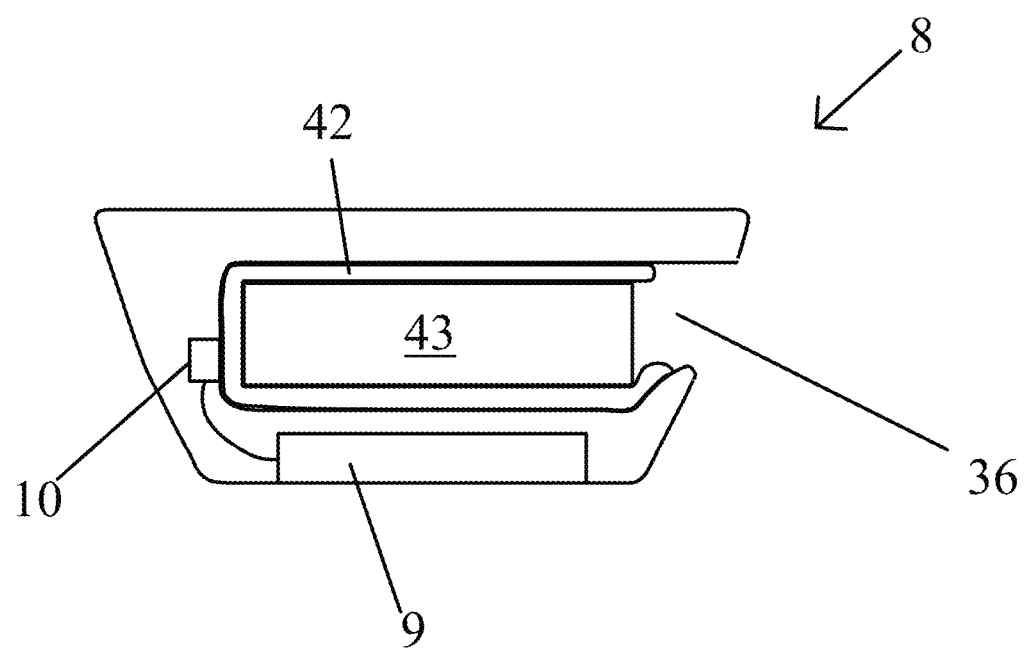
FIG. 3B shows a cross-sectional view of a payload container in another embodiment of the present invention.

FIGS. 3A and 3B shows examples of payload containers 8 in embodiments of the present invention. A payload container 8, containing the biologic payload (e.g. biologic-based medicine), is designed to fit specifically in place within an insulated shipping container. The payload container 8 in FIG. 3A includes a top 35, which may be a clam shell or other opening. The payload container 8 also includes a cavity 36 for insertion and storage of the biologic based material. In FIG. 3B, the cavity 36 is located so that the primary payload container 43 (which contains the biologic being transported) is inserted horizontally into the payload container 8. In other embodiments, the cavity 36 or storage volume is configured differently, for example, as a cavity formed by a bottom and sidewalls of the payload container 8. The cavity 36 is also preferably lined with packing material 42 (for example bubble wrap, dunnage, or cushion foam) to protect the payload from mechanical vibration, shock, or other forms of stress during transit.

As shown in FIGS. 3A and 3B, the payload container 8 preferably includes a communications device 9 which monitors a range of parameters of conditions of the payload and transmits the information regarding these conditions to a long-range communications device 3, which itself is embedded in the insulated shipping container (see FIGS. 1A through 1C). Some of these parameters include, but are not limited to, location, temperature, pressure, humidity, tilt, exposure to light, acceleration, battery life, and communication signal strength. For example, the payload container 8 may include an RFID tag or other communications device to identify the location of the payload container 8. The payload container 8 may also contain a temperature sensor 10, such as a thermocouple. The temperature sensor is connected to the communications device 9, preferably either by direct wiring or wireless communication.

The communication device 9 may transmit information to other devices utilizing near field communication methods. In some embodiments, the payload communications device 9 is a near field or close proximity electronic communication device that provides location and temperature information and may communicate using Bluetooth®, Wi-Fi or other forms of near field communication (NFC). Some near field or close proximity electronic communications devices 9 that could be used include, but are not limited to, active RFID devices, RFID tags, RF transmitters, iBeacon™ transmitters, ZigBee® transmitters, Bluetooth transmitters, Wi-Fi radios, and other wireless transmitters.

When the insulated shipping container reaches its destination, the payload container 8 is often unpacked and separated from the insulated shipping container 1. At that point, prior art methods of tracking an insulated shipping container fail, since the payload container 8 is no longer associated with the shipping container. But, the payload container 8 still needs to be monitored, since the temperature of the payload container 8 may increase to a temperature point above viable temperatures for the biologic. In addition, the payload container 8 would likely need to arrive at a specific location in a certain time period.

A payload container 8 that includes an internal communications device 9 allows for the tracking of the payload container 8 itself, after it reaches its general destination (such as the dock of a hospital). A temperature sensor 10, such as a thermocouple, may also be included in the payload container 8, to continue to monitor the temperature of the payload container 8 even after it has been removed from the insulated shipping container 1. The communications device 9 can communicate with a network, allowing communication to take place between the payload container 8 and a network associated with the destination. For example, the communications device 9 may communicate with a mobile device, which communicates wirelessly with a hospital network. The payload container 8 of the present invention provides autonomy of the payload container 8 within the facility, preferably for at least an hour or two.

Rather than losing the ability to track the payload container 8 when it reaches the dock or another location where it is unpacked from the insulated shipping container, the payload container 8 may be tracked until it gets to the patient. The payload container 8 preferably includes electronics 9 that transmit location and, in preferred embodiments, also temperature 10. Since the payload container 8 still transmits information after it is unpacked, information is still received up until the biologic has reached the patient's bedside or the doctor attending to the patient.

While the payload container 8 is shown as specific shapes in the figures, any payload container capable of safely housing the biologic of interest may be used.

A logistics system preferably acts as a hub for the information flow between the insulated container, the payload container and the users who may be involved in the shipping, receiving and use of the materials which are being shipped. These users include, but are not limited to, clinicians and patients. The logistics system preferably includes a communications network having the ability to prevent the completion of an air bill for the shipment of a temperature sensitive shipment in the case that the shipment pack out has not been performed properly.

Figure 4A:
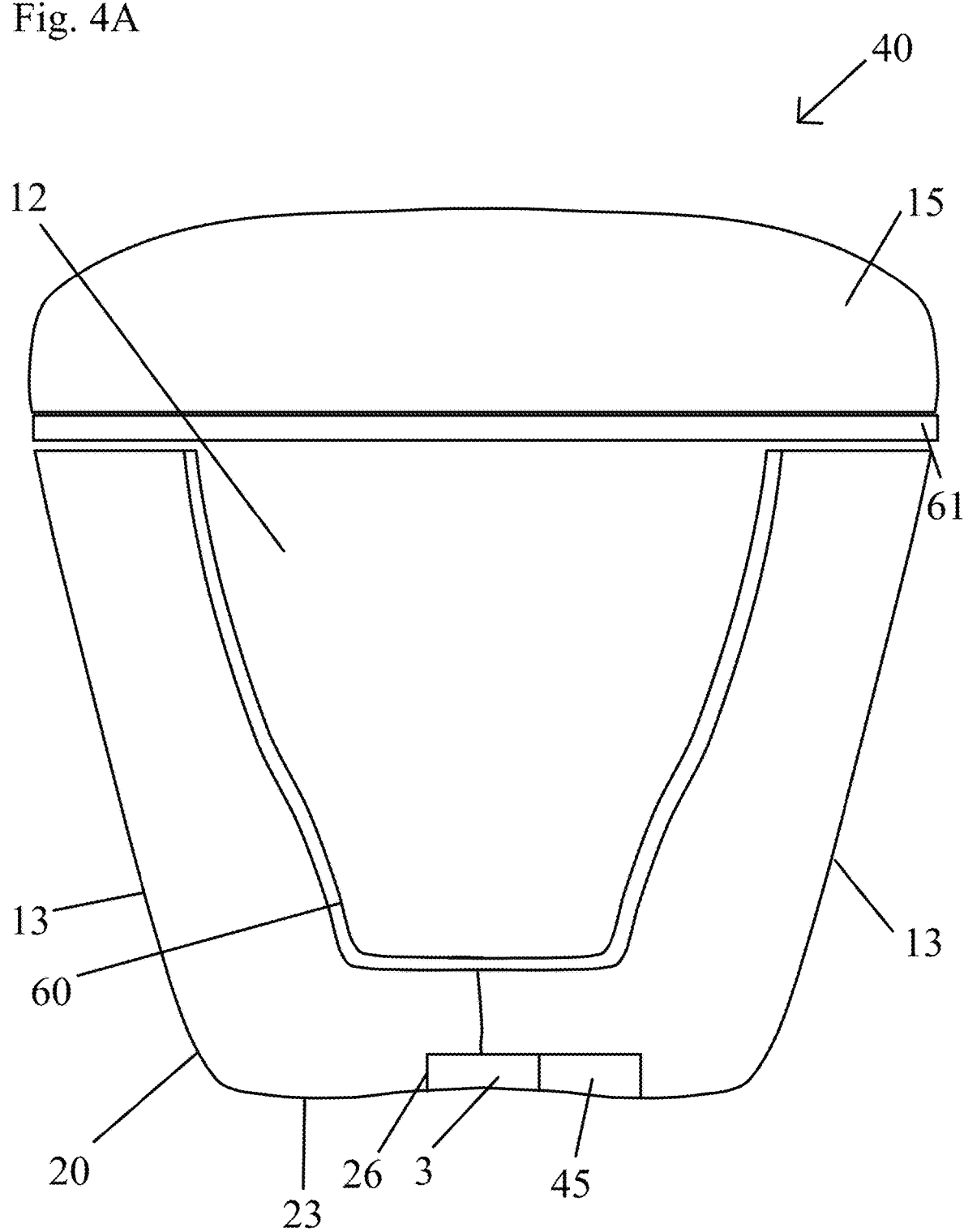
FIG. 4A shows an insulated shipping container with a communications device plus shielding in an embodiment of the present invention.
Figure 4B:
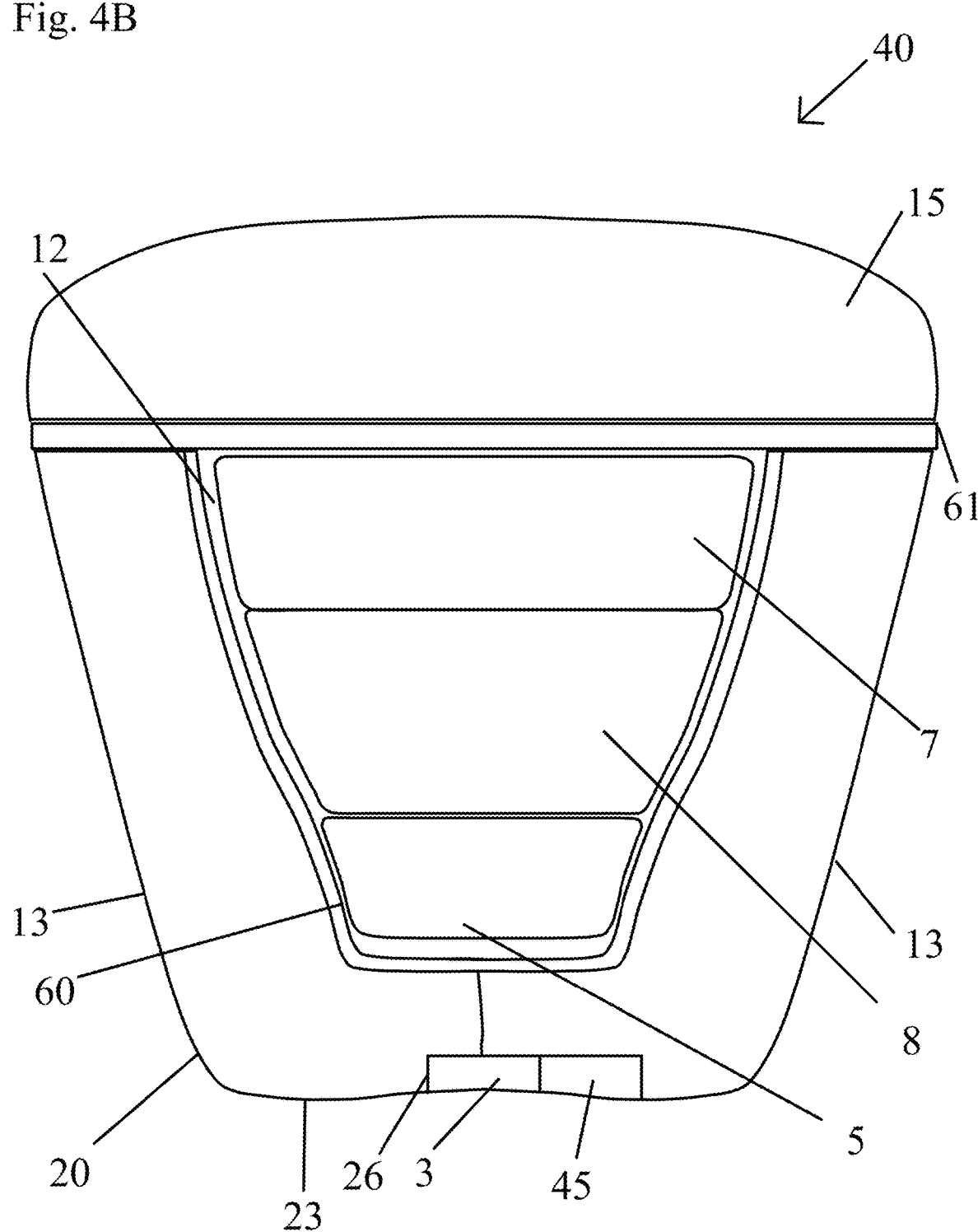
FIG. 4B shows the insulated shipping container of FIG. 4A, packed with insulating materials and the payload container.

FIG. 4A shows a shipping or storage container 40 with a communications device 3 and a cavity 12 for receiving a payload container 8. FIG. 4B shows the insulated shipping or storage container of FIG. 4A, packed with insulating materials 5, 7, and a payload container 8 without its own separate shielding. The insulated shipping container 40 includes a bottom or body 20 and a top or lid 15. The body 20 includes a base 23 and sidewalls 13 that extend up from the base 23. The body 20 defines an open storage volume or cavity 12. The top 15 is removable to provide access to the storage volume 12. When the top 15 is placed on the body 20, the storage volume 12 is closed. The top 15, the base 23 and the sidewalls 13 preferably include multiple layers of insulating materials.

The communications device 3 is preferably housed in a cavity 26 in the base 23 of the insulated shipping container 40. In preferred embodiments, the communications device 3 is a long-range communications device that uses near field electronic communication to provide information and may communicate using Bluetooth®, Wi-Fi or other forms of near field communication (NFC). In some embodiments, the communications device 3 includes GPS, a cellular modem, and/or other wireless communication devices. The communication device 3 may transmit information to other devices utilizing near field communication methods. Some examples of these communications devices include, but are not limited to, cellular communication devices (e.g.—cellular phones, cellular modems, code division multiple access systems, global system for mobile communications, and other cellular portions of the spectrum), RF transmitters, active RFID devices, RFID tags, iBeacon™ transmitters, ZigBee® transmitters, Bluetooth® transmitters, Wi-Fi radios, other wireless transmitters, or other near field communication signals or devices. In some embodiments, the materials attenuate ionizing radiation (e.g.—X-ray radiation such as airport screening devices).

The wireless communication devices are preferably permanently integrated into the base 23 of the container 40. The container 40 also includes shielding 60 on the interior of the cavity 26 and shielding 61 on the underside of the lid 15 of the container 40. The shielding 60 and 61 may be located anywhere between the communications device 3 and the payload container 8. For example, while the shielding 60 is shown on all of the sidewalls in FIG. 4A, the shielding may only be located in a position between the communications device 3 and the payload container 8 received within the cavity 12. In some of these embodiments, the shielding 60 is a plate located between the communications device 3 and the payload container 8. If plates are used, they are placed so that they still permit the cellular modem, or other communications device, to transmit. In other embodiments, a plate may be placed within the cavity 26 in a location that shields the payload container 8 from the communications device 3, but still permits transmission of the communications device 3 to a remote location.

The shielding 60, 61 may be made of any shielding material that is able to block the radiation emitting from the communications device, including, but not limited to, lead, aluminum, bronze, copper, nickel, zinc, another metal, conductive plastics, or carbon based materials. The form of the shielding 60, 61 is preferably selected from the group consisting of plates, coatings, inserts, sprayed on liners, mesh, foil, foam, paints, inks, solid plates or pieces, or a film adhesive. The sprayed on liner may be made of electric arc sprayed on zinc. If plates are used, they are preferably made from lead or another metal, and they are placed so that they still permit the communications device, to transmit. If coatings are used, the coatings chosen are preferably made of materials that allow X-rays to pass through so that all interior spaces of the shipping container are still visible. Any combinations of materials and types of shielding may be used.

The insulated shipping container 40 also preferably includes a power compartment 45, which provides power to the electronics in the insulated shipping container 40. In some preferred embodiments, the power compartment 45 is a battery compartment, which contains a battery pack. The battery pack preferably powers the communications device 3. While the power compartment 45 is shown on the bottom of the base 23 of the insulated shipping container 40 in the Figures, the power compartment 45 may be in alternative locations, and is preferably connected (via wiring or wirelessly) to the communications device 3.

The communications device 3 permits the insulated shipping container to communicate to an outside source, including, but not limited to, a cloud-based database or program, device computers, server computers, or other devices. It should be noted that the term "outside" means with a device other than present within the shipping or storage container. While the communications device 3 is shown placed in the base 23 of the shipping container 40 in FIG. 4A, the communications device may be in any location where it does not interfere with other components of the container.

This communication device 3 communicates to an outside source including, but not limited to, a cloud-based database or program, device computers, server computers, or other devices. The outside source can also determine whether certain parameters are not within appropriate ranges and notify users.

Figure 4C:
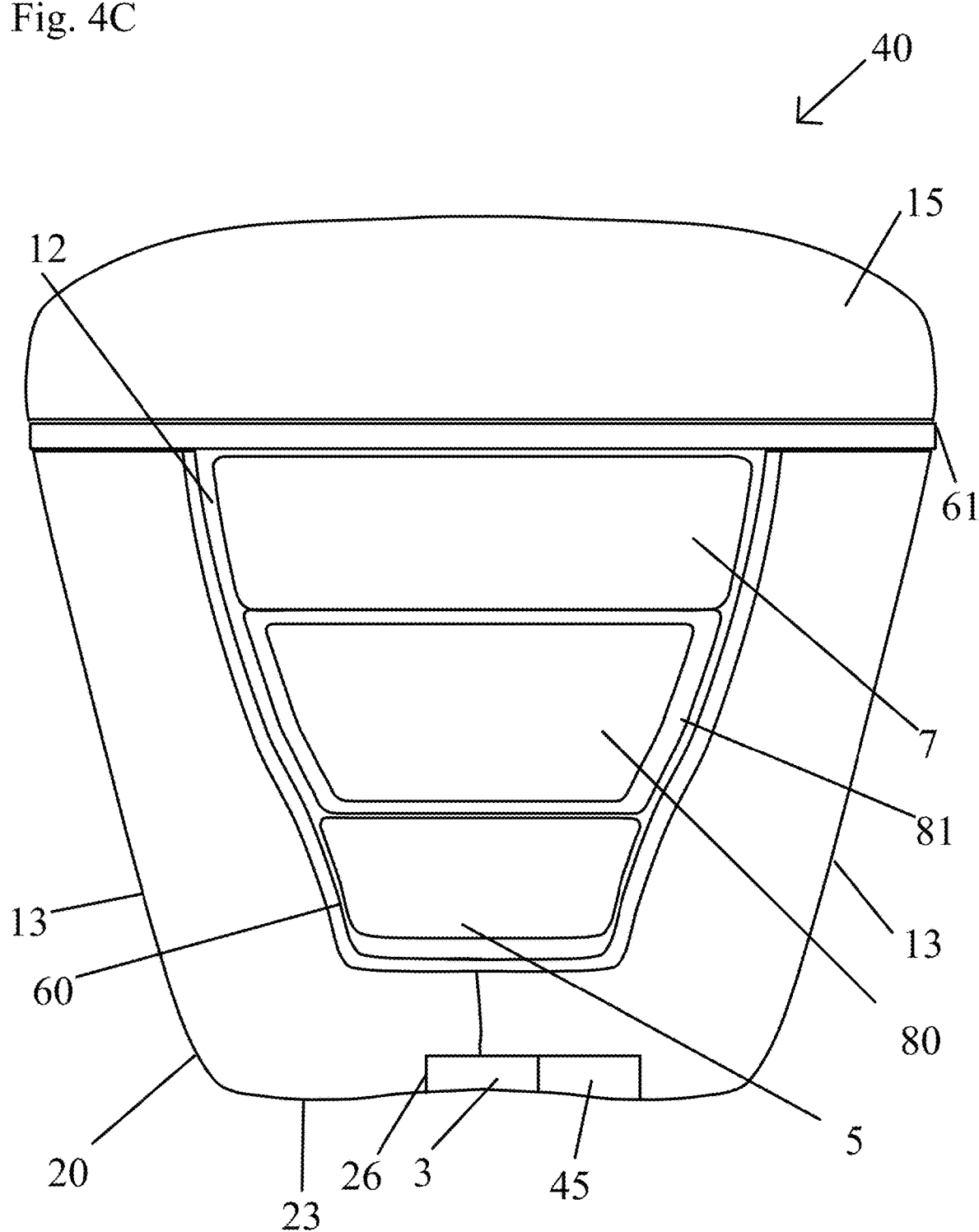
FIG. 4C shows the insulated shipping container of FIG. 4A, packed with insulating materials and a payload container, which is also shielded.

FIG. 4C shows the insulated shipping or storage container 40 of FIG. 4A, packed with insulating materials and a shielded payload container 80. The shielding 81 may form the exterior of the payload container 80, or may line one or more of the interior walls of the payload container 80. In preferred embodiments, the shielding 81 is located along the entire perimeter of the payload container 80. However, the shielding 81 may alternatively only be located on some of the walls, preferably those that are located between the communications device 3 and the payload container 80 when the payload container 80 is packed in the shipping container 40. The shielded payload container 80 could alternatively be used in an insulated shipping container 40 without its own shielding.

The shielding 81 in the payload container 80 may be made of any shielding material that is able to block the radiation emitting from the communications device, including, but not limited to, lead, aluminum, bronze, copper, nickel, zinc, another metal, conductive plastics, or carbon based materials. The form of the shielding is preferably selected from the group consisting of plates, coatings, inserts, sprayed on liners, mesh, foil, foam, paints, inks, solid plates or pieces, or a film adhesive. The sprayed on liner may be made of electric arc sprayed on zinc. If plates are used, they are preferably made from lead or another metal and are placed so that they still permit the communications device, to transmit, if one is present in the payload container. If coatings are used, the coatings chosen are preferably made of materials that allow X-rays to pass through so that all interior spaces of the shipping container are still visible. While the shielding is shown within the container 40 of FIG. 4A, both the shielding and the sensors for detecting radiation exposure (see FIGS. 6-7 below) could be used in combination with any of the other embodiments described herein.

Figure 5:
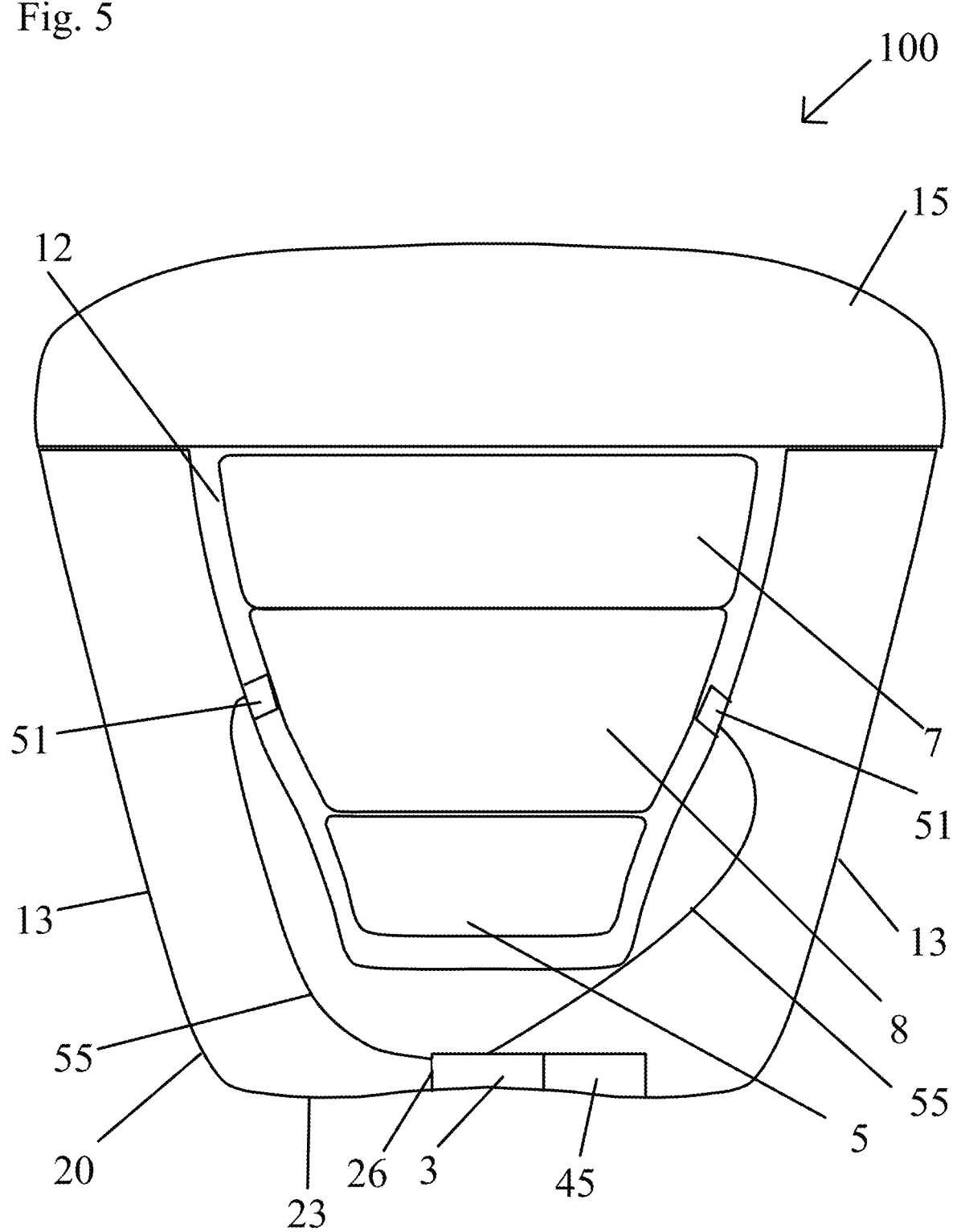
FIG. 5 shows an insulated shipping container with a communications device plus at least one sensor to detect non-ionizing radiation exposure in an embodiment of the present invention. The insulated shipping container is packed with insulating materials and the payload container. The insulated shipping container could also contain shielding (as shown in FIGS. 4A to 4C) to shield the payload container from the communications device.

FIG. 5 shows an insulated shipping or storage container 100 with a communications device 3 (e.g.—a cellular modem or other near field communications device) plus at least one non-ionizing radiation sensor 51 to detect RF energy or other near field radiation exposure. The non-ionizing radiation sensor 51 may be a radiation detector. One example of a radiation detector is a modular device with a wired sensor incorporating a radiation detector diode (such as the SPD9441 Radiation Detector PIN Diode, Solid State Devices, Inc., La Mirada, Calif.). Another example is a USB spectrum analyzer for detecting and measuring emitted electromagnetic radiation from cell phones or other sources (such as the TSA6G1 USB Mini Spectrum Analyzer, Triarchy Technologies Corp., Surrey, British Columbia). In preferred embodiments, the communications device 3 is a long-range communications device that uses near field electronic communication to provide information and may communicate using Bluetooth®, Wi-Fi or other forms of near field communication (NFC). In some embodiments, the communications device 3 includes GPS, a cellular modem, and/or other wireless communication devices. The communication device 3 may transmit information to other devices utilizing near field communication methods. Some examples of these communications devices include, but are not limited to, cellular communication devices (e.g.—cellular phones, cellular modems, code division multiple access systems, global system for mobile communications, and other cellular portions of the spectrum), RF transmitters, active RFID devices, RFID tags, iBeacon™ transmitters, ZigBee® transmitters, Bluetooth® transmitters, Wi-Fi radios, other wireless transmitters, or other near field communication signals or devices. In some embodiments, the materials attenuate ionizing radiation (e.g.—X-ray radiation such as airport screening devices).

While two sensors 51 are shown in the figure, one sensor or more than two sensors could alternatively be used. The sensors 51 are preferably at least partially embedded or fully embedded into one or more of the walls of an insulated shipping or storage container. In one embodiment, the container 100 also preferably includes wiring 55 to connect the sensors 51 to the communications device 3. In other embodiments, the sensors 51 are wireless. In both wired and wireless embodiments, the sensors 51 preferably communicate with the communications device 3 to preferably get the data transmitted to the cloud or another wireless location. The insulated shipping container 100 is packed with insulating materials 5, 7 and the payload container 8. The insulated shipping container 100 could also contain shielding (as shown in FIGS. 4A to 4C) to shield the payload container 8 from the communications device 3.

Figure 6:
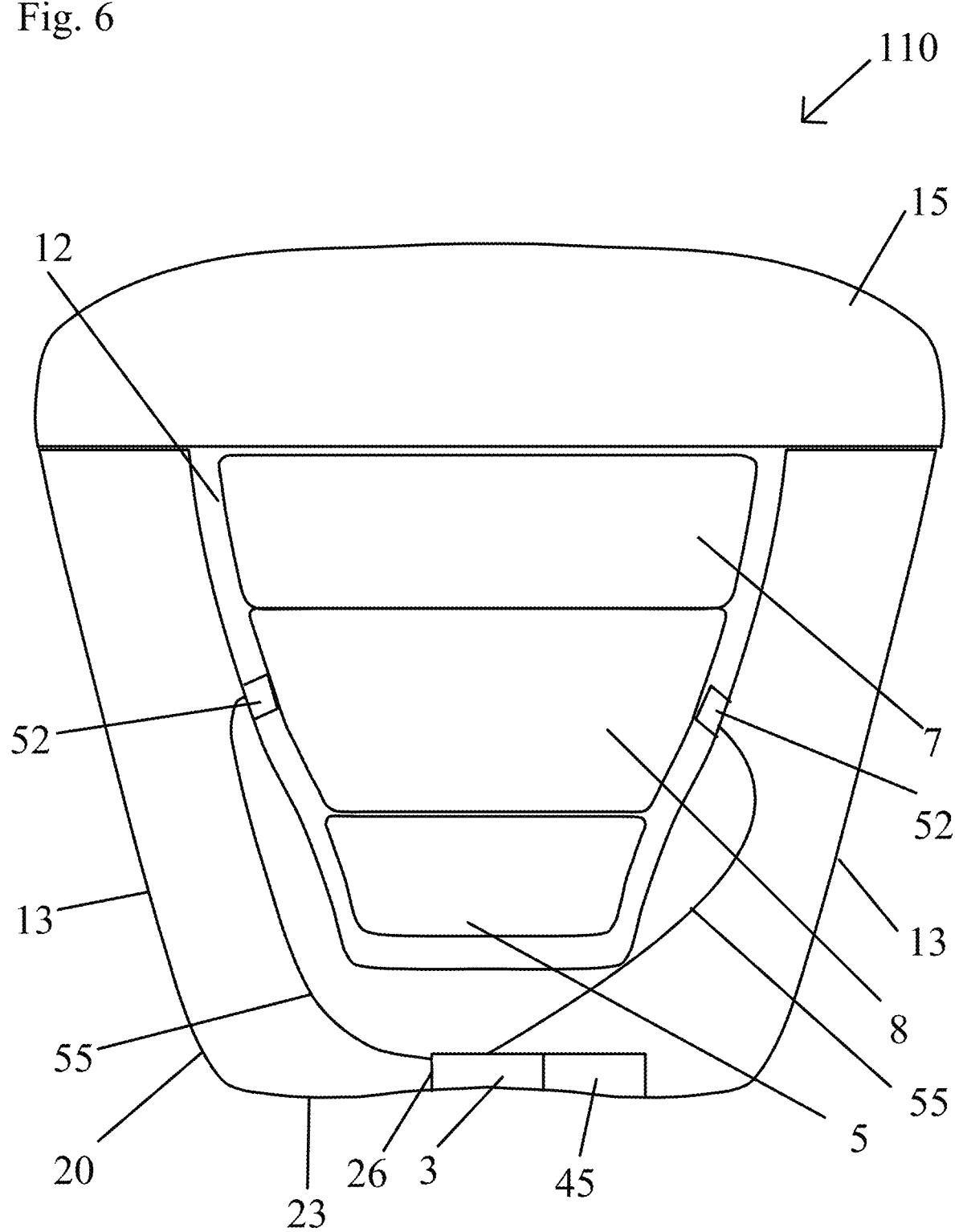
FIG. 6 shows an insulated shipping container with a communications device plus at least one sensor to detect ionizing radiation exposure in an embodiment of the present invention. Although a communications device is shown in this figure, simple shipping or storage containers without these devices could also utilize the radiation sensors shown in this figure. In the figure, the insulated shipping container is packed with insulating materials and the payload container.

FIG. 6 shows an insulated shipping container 110 with a communications device 3 (e.g.—a cellular modem or other near field communications device) plus at least one sensor 52 to detect ionizing radiation, such as X-ray exposure. The ionizing radiation sensor 52 may be a radiation detector. One example of a radiation detector is a modular device with a wired sensor incorporating a radiation detector diode (such as the SPD9441 Radiation Detector PIN Diode, Solid State Devices, Inc., La Mirada, Calif.). Another example is a USB spectrum analyzer for detecting and measuring emitted electromagnetic radiation from cell phones or other sources (such as the TSA6G1 USB Mini Spectrum Analyzer, Triarchy Technologies Corp., Surrey, British Columbia). In preferred embodiments, the communications device 3 is a long-range communications device that uses near field electronic communication to provide information and may communicate using Bluetooth®, Wi-Fi or other forms of near field communication (NFC). In some embodiments, the communications device 3 includes GPS, a cellular modem, and/or other wireless communication devices. The communication device 3 may transmit information to other devices utilizing near field communication methods. Some examples of these communications devices include, but are not limited to, cellular communication devices (e.g.—cellular phones, cellular modems, code division multiple access systems, global system for mobile communications, and other cellular portions of the spectrum), RF transmitters, active RFID devices, RFID tags, iBeacon™ transmitters, ZigBee® transmitters, Bluetooth® transmitters, Wi-Fi radios, other wireless transmitters, or other near field communication signals or devices. In some embodiments, the materials attenuate ionizing radiation (e.g.—X-ray radiation such as airport screening devices).

While two sensors 52 are shown in the figure, one sensor or more than two sensors 52 could alternatively be used. Although a communications device 3 is shown in this figure, simple shipping containers without these devices could also utilize the radiation sensors 52 shown in this figure. The sensors 52 are preferably at least partially embedded or fully embedded into one or more of the walls of an insulated shipping container. In one embodiment, the container also preferably includes wiring 55 to connect the sensors 52 to the communications device 3. In other embodiments, the sensors 52 are wireless. In both wired and wireless embodiments, the sensors 52 preferably communicate with the communications device 3 to preferably get the data transmitted to the cloud or another wireless location. The insulated shipping container 110 is packed with insulating materials 5, 7 and the payload container 8. The insulated shipping container 110 could also contain shielding (as shown in FIGS. 4A to 4C) to shield the payload container 8 from the communications device 3 if that shielding did not interfere with X-ray equipment necessary to scan the biologic being shipped.

The dosimeters/sensors 52 are connected to the electronics of the insulated shipping container 110 (either through wiring or wirelessly) and the sensors 52 protrude into the payload cavity 12 in FIG. 6. In other embodiments (not shown), since the X-rays pass through the entire container during a TSA or other scan, the sensors 52 could be built into the electronics of the container or are located elsewhere in the container 110. For example, the dosimeter/sensor 52 could have separate electronics or may have electronics which are part of the communications device or other existing monitoring electronics in an insulated shipping container.

Insulated shipping containers could alternatively utilize both non-ionizing radiation sensors 51 and ionizing radiation sensors 52, to sense exposure of multiple types of radiation.

Figure 7:
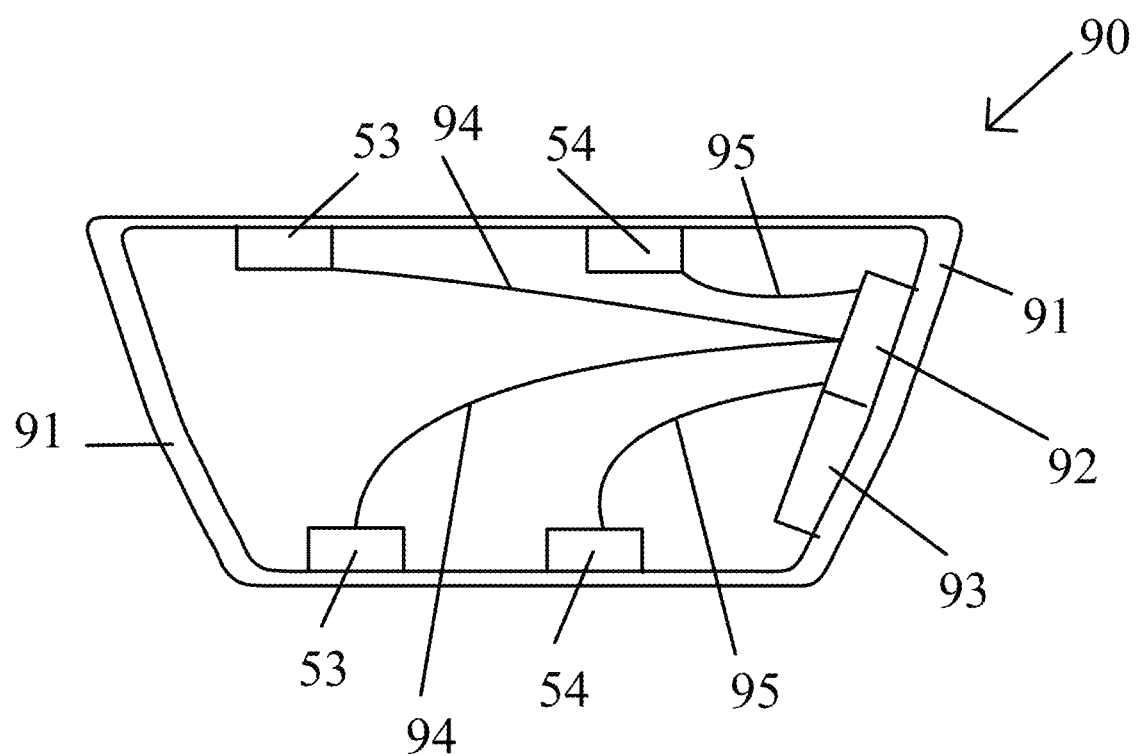
FIG. 7 shows a payload container with shielding and radiation sensors.

FIG. 7 shows a payload container 90 with shielding 91 and non-ionizing radiation sensors 53 and ionizing radiation sensors 54. Radiation sensors 53 preferably sense exposure to near field radiation, such as RF energy, and radiation sensors 54 preferably sense exposure to X-ray radiation. In some embodiments, the payload container 90 also preferably includes wiring 94 to connect the sensors 53 to the communications device 92 and wiring 95 to connect the sensors 54 to the communications device 92. In other embodiments, the sensors 53 and/or 54 are wireless. In both wired and wireless embodiments, the sensors 53, 54 preferably communicate with the communications device 92 to preferably get the data transmitted to the cloud or another wireless location.

In preferred embodiments, the communications device 92 uses near field electronic communication to provide information and may communicate using Bluetooth®, Wi-Fi or other forms of near field communication (NFC). In some embodiments, the communications device 92 includes GPS, a cellular modem, and/or other wireless communication devices. The communication device 92 may transmit information to other devices utilizing near field communication methods. Some examples of these communications devices include, but are not limited to, cellular communication devices (e.g.—cellular phones, cellular modems, code division multiple access systems, global system for mobile communications, and other cellular portions of the spectrum), RF transmitters, active RFID devices, RFID tags, iBeacon™ transmitters, ZigBee® transmitters, Bluetooth® transmitters, Wi-Fi radios, other wireless transmitters, or other near field communication signals or devices. In some embodiments, the materials attenuate ionizing radiation (e.g.—X-ray radiation such as airport screening devices).

The shielding 91 may form the exterior of the payload container 90, or may line one or more of the interior walls of the payload container 90. In preferred embodiments, the shielding 91 is located along the entire perimeter of the payload container 90. However, the shielding 91 may alternatively only be located on some of the walls, preferably those that would be located between the communications device 3 of the insulated shipping or storage container and the payload container 90 when the payload container 90 is packed in the shipping container. In other embodiments (not shown), the shielding surrounds a communications device 92 and/or a power compartment 93 within the payload container 90 or is located between the communications device 92 and the payload in the payload container 90. For example a shielding plate could be placed between the communications device 92 and the payload in the payload container 90. The plate is placed so that it still permits the cellular modem or other communications device, to transmit. The shielded payload container 90 could be used in an insulated shipping container 40 with its own shielding (see FIG. 4A).

The shielding 91 in the payload container 90 may be made of any shielding material that is able to block the radiation emitting from the communications device, including, but not limited to, lead, aluminum, bronze, copper, nickel, zinc, another metal, conductive plastics, or carbon based materials. The form of the shielding is preferably selected from the group consisting of plates, coatings, inserts, sprayed on liners, mesh, foil, foam, paints, inks, solid plates or pieces, or a film adhesive. The sprayed on liner may be made of electric arc sprayed on zinc. If plates are used, they are preferably made from lead or another metal and are placed so that they still permit the cellular modem or other communications device, if present in the payload container, to transmit. If coatings are used, the coatings chosen are preferably made of materials that allow X-rays to pass through so that all interior spaces of the shipping container are still visible. While the shielding is shown with the container of FIG. 1A, both the shielding and the sensors for detecting radiation exposure (see FIGS. 6-7 below) could be used in combination with any of the other embodiments described herein.

While shielding 91 and sensors 53, 54 which detect multiple types of radiation (RF energy sensors 53 and X-ray sensors 54) are all shown in this figure, the payload container 90 may include only one of these components, or any combination of these components. In addition, as discussed above, the shielding 91 of the payload container 90 could be located on the exterior or in the interior of the payload container 90.

For example, in some embodiments, the payload container includes the sensors 53, 54, but no shielding. In some of these embodiments, the payload container does not have a communications device or power compartment, the sensors 53, 54 are wireless, and communicate with the communication device in an insulated shipping container that has shielding. That communications device is able to store and transmit the exposure data to the cloud.

In other embodiments, the payload container includes only sensors 54, to sense the X-ray exposure of biologics being subject to TSA scans. In some of these embodiments, the payload container does not include any communications devices or a power compartment, and the X-ray sensors are wireless and communicate with the communications device in an insulated shipping container that has shielding. That communications device is able to store and transmit the exposure data to the cloud.

Although the payload container 90 is shown as a particular shape in FIG. 7, any shaped payload container 90 could include sensors 53, sensors 54, and or shielding 91. The payload container 90 shown in FIG. 7, or any variation of the payload container 90, could be used in any of the embodiments described herein.

Figure 8:
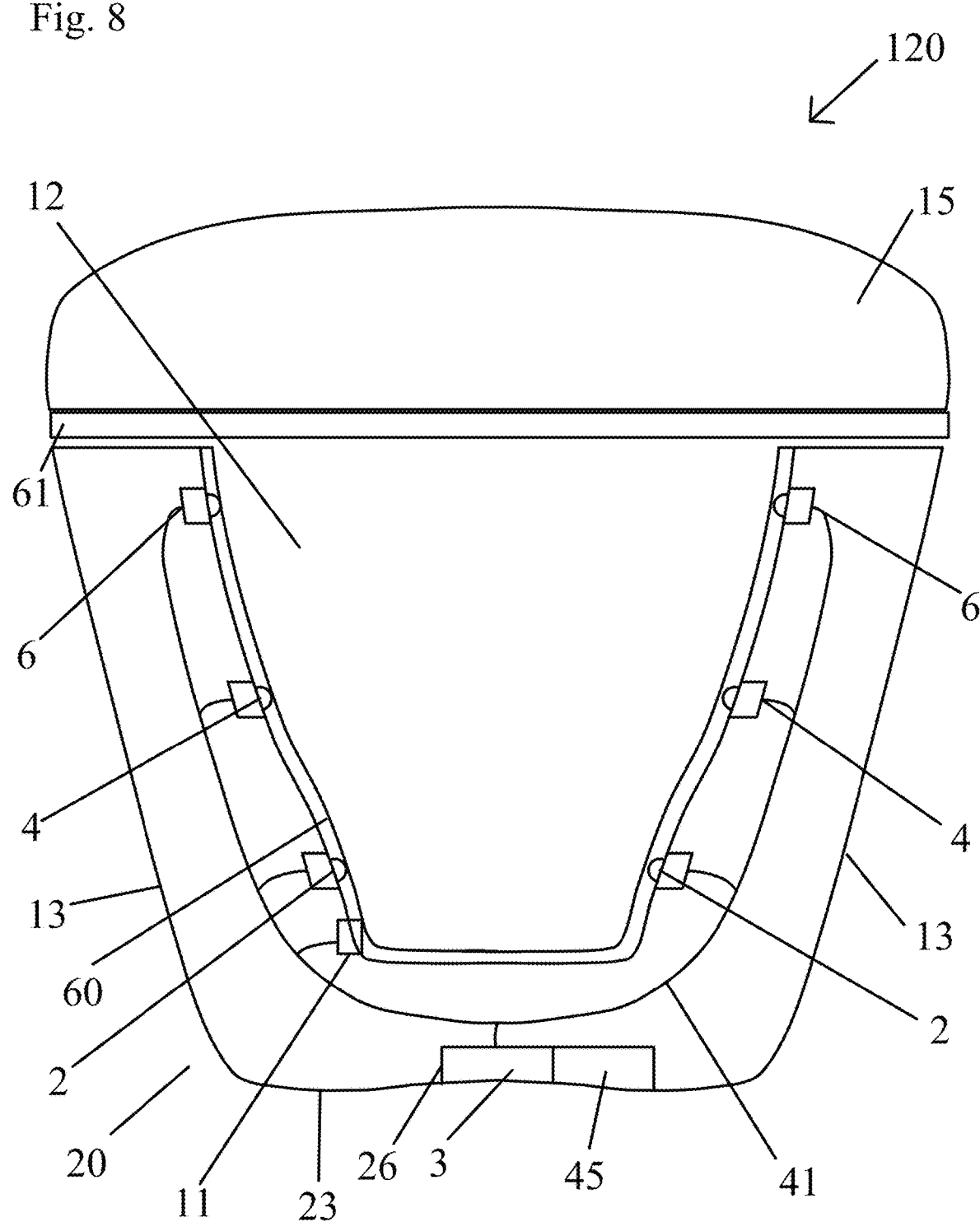
FIG. 8 shows a shipping container in an embodiment of the present invention, with the shielding shown in FIG. 4 and the switches and/or sensors shown in FIG. 1.

The shielding and radiation exposure sensors described in FIGS. 4 through 7 could be used in combination with any of the other shipping container and logistics embodiments described in this application. For example, FIG. 8 shows a shipping container 120 in an embodiment of the present invention, with the shielding 60, 61, shown in FIG. 4 and the switches and/or sensors 2, 4, 6 shown in FIG. 1.

The embodiments described herein, particularly the shielding and monitoring embodiments described with respect to FIGS. 4-8 (but also the other embodiments described herein) could be used in combination with any insulated shipping container available. For example, the devices in US Patent Publication 2014/0138392, entitled "Contents Rack for Use in Insulated Storage Containers", published May 22, 2014, herein incorporated by reference, could use the shielding and monitoring embodiments as described herein.

All of the patent and nonpatent references discussed herein are incorporated herein by reference.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An insulated shipping or storage container comprising:
an insulated container body comprising a bottom and sidewalls extending from the bottom of the body, a first main cavity, and a second cavity, wherein the bottom and sidewalls form the first main cavity;
a removable top that fits onto the insulated container body, sealing the first main cavity;
a long-range communications device located within the second cavity of the insulated container body, to transmit information to a communications network; and
a first shielding material lining at least a portion of the bottom and sidewalls of the insulated container body, wherein the first shielding material is selected from the group consisting of: lead, zinc, aluminum, bronze, copper, nickel, a conductive plastic, a metal that does not block X-rays, and a carbon based material.

2. The insulated shipping or storage container of claim 1, further comprising a second shielding material lining an interior of the removable top.

3. The insulated shipping or storage container of claim 1, wherein the first shielding material comprises a shielding type selected from the group consisting of: a coating, a plate, a sprayed on liner, an insert, mesh, foil, foam, paint, ink, and a film adhesive.

4. The insulated shipping or storage container of claim 1, wherein the first shielding material shields the first main cavity from, or attenuates, external radiation, the external radiation consisting of one or more of radio waves, electromagnetic radiation, and non-ionizing radiation.

5. The insulated shipping or storage container of claim 1, wherein the first shielding material does not block X-rays.

6. The insulated shipping or storage container of claim 1, wherein the first shielding material is located between the long-range communications device and the first main cavity.

7. The insulated shipping or storage container of claim 1, further comprising at least one sensor operatively connected to the long-range communications device and located within the first main cavity or at least partially embedded in the bottom or sidewalls of the insulated container body, wherein the sensor senses exposure to radiation within the first main cavity.

8. The insulated shipping or storage container of claim 7, wherein the sensor senses exposure to X-ray radiation or radio frequency energy.

9. An insulated shipping or storage container comprising:
an insulated container body comprising a bottom and sidewalls extending from the bottom of the body, a first main cavity and a second cavity, wherein the bottom and sidewalls form the first main cavity;
a removable top that fits onto the insulated container body; sealing the first main cavity;
a long-range communications device located within the second cavity of the insulated container body, to transmit information to a communications network; and
a shielding material lining at least a portion of the second cavity,
wherein the shielding material is selected from the group consisting of: lead, zinc, aluminum, bronze, copper, nickel, a conductive plastic, a metal that does not block X-rays, and a carbon based material.

10. The insulated shipping or storage container of claim 9, wherein the shielding material comprises a shielding type selected from the group consisting of a coating, a plate, a sprayed on liner, an insert, mesh, foil, foam, paint, ink, and a film adhesive.

11. The insulated shipping or storage container of claim 9, wherein the shielding material shields the first main cavity from, or attenuates, external radiation, the external radiation consisting of one or more of radio waves, electromagnetic radiation, and non-ionizing radiation.

12. The insulated shipping or storage container of claim 9, wherein the shielding material does not block X-rays.

13. The insulated shipping or storage container of claim 9, wherein the shielding material is located between the long-range communications device and the first main cavity.

14. The insulated shipping or storage container of claim 9, further comprising at least one sensor operatively connected to the long-range communications device and located within the first main cavity or at least partially embedded in the bottom or sidewalls of the insulated container body, wherein the sensor senses exposure to radiation within the first main cavity.

15. The insulated shipping or storage container of claim 14, wherein the sensor senses exposure to X-ray radiation or radio frequency energy.

16. A thermally insulated payload container for storing biologics, the payload container comprising shielding material lining at least a portion of a body of the payload container to protect an internal cavity of the payload container from exposure to external radiation, wherein the shielding material is selected from the group consisting of: lead, zinc, aluminum, bronze, copper, nickel, a conductive plastic, a metal that does not block X-rays, and a carbon based material.

17. The payload container of claim 16, wherein the shielding material is a type selected from the group consisting of a coating, a plate, a sprayed on liner, an insert, mesh, foil, foam, paint, ink, and a film adhesive.

18. The payload container of claim 17, wherein the coating is chosen such that it allows X-rays to pass through the coating.

19. The payload container of claim 16, wherein the shielding material is located between a long-range communications device and a main cavity in the payload container.

\* \* \* \* \*